US008777970B2

(12) United States Patent
Kim et al.

(10) Patent No.: US 8,777,970 B2
(45) Date of Patent: Jul. 15, 2014

(54) SLOT DRIVE TYPE ANASTOMOSIS DEVICE

(75) Inventors: Cheol Woong Kim, Seoul (KR); Dae Won Jee, Seoul (KR); Gi Bong Han, Seoul (KR)

(73) Assignee: Triple-C Medical Corporation, Seoul (KR)

( * ) Notice: Subject to any disclaimer, the term of this patent is extended or adjusted under 35 U.S.C. 154(b) by 589 days.

(21) Appl. No.: 13/093,065

(22) Filed: Apr. 25, 2011

(65) Prior Publication Data

US 2011/0319916 A1    Dec. 29, 2011

(30) Foreign Application Priority Data

Jun. 25, 2010   (KR) .................. 10-2010-0060286

(51) Int. Cl.
*A61B 17/11*   (2006.01)
(52) U.S. Cl.
USPC ........... 606/153; 606/148; 606/150; 606/151; 606/170; 606/185; 606/220; 606/215; 606/139; 227/175.1; 227/180.1
(58) Field of Classification Search
USPC ......... 606/104, 139, 143, 144, 148, 150, 151, 606/153, 158, 170, 185, 205; 227/175.1, 227/180.1
See application file for complete search history.

(56) References Cited

U.S. PATENT DOCUMENTS

| | | | | |
|---|---|---|---|---|
| 3,316,914 A | * | 5/1967 | Collito | 606/150 |
| 4,607,637 A | * | 8/1986 | Berggren et al. | 606/153 |
| 4,624,257 A | * | 11/1986 | Berggren et al. | 606/153 |
| 4,917,091 A | * | 4/1990 | Berggren et al. | 606/153 |
| 6,514,263 B1 | * | 2/2003 | Stefanchik et al. | 606/144 |
| 8,313,013 B2 | * | 11/2012 | Kuester et al. | 227/175.1 |

FOREIGN PATENT DOCUMENTS

| | | |
|---|---|---|
| EP | 1842495 | 10/2007 |
| KR | 10-2010-0020183 | 2/2010 |
| KR | 10-2010-0020556 | 2/2010 |
| KR | 10-2010-0034854 | 4/2010 |

OTHER PUBLICATIONS

English language abstract of KR 10-2010-0034854.
English language abstract of KR 10-2010-0020556.
English language abstract of KR 10-2010-0020183.

* cited by examiner

*Primary Examiner* — Vy Q Bui
(74) *Attorney, Agent, or Firm* — Rabin & Berdo, P.C.

(57) ABSTRACT

Provided is an anastomosis device including a first head holding a first anastomosis ring, a second head holding a second anastomosis ring, a first guide bar connected to the first head and switching a release position and a standby position to each other, wherein the first guide bar includes a first rotation groove, a second guide bar connected to the second head and switching the release position and the standby position to each other, wherein the second guide bar includes a second rotation groove, and a rotation driver moving approximately in a parallel direction to the first and second guide bars and including a first guide protrusion and a second guide protrusion, which move along the first and second rotation grooves, respectively.

14 Claims, 27 Drawing Sheets

SLOT DRIVE TYPE ANASTOMOSIS DEVICE

CROSS-REFERENCE TO RELATED APPLICATIONS

This U.S. non-provisional patent application claims priority under 35 U.S.C. §119 to Korean Patent Application No. 10-2010-0060286, filed on Jun. 25, 2010, the entire contents of which are hereby incorporated by reference.

BACKGROUND

The present invention herein relates to an anastomosis device, and more particularly, to an anastomosis device including anastomosis rings that are coupled to perform an anastomosis on tubular body structures.

Tubular body structures, such as blood vessels or intestines, can be connected to each other by joining their ends together using suture techniques. However, this method requires much time in mastering the suture techniques.

Anastomosis rings may be used to address these limitations. FIG. 26 is a perspective view illustrating an anastomosis ring installed on a tubular body structure such as a blood vessel. FIG. 27 is a perspective view illustrating an anastomosis using anastomosis rings. Referring to FIG. 26, an end of a first tubular body structure T1 passes through a first anastomosis ring R1, and is turned inside out on a surface of the first anastomosis ring R1. First fixing pins P1 protruding from the surface of the first anastomosis ring R1 pass through the end of the first tubular body structure T1 to fix the first tubular body structure T1 to the first anastomosis ring R1. Accordingly, the removal of the first tubular body structure T1 from the first anastomosis ring R1 is prevented, the coupling of intimae is facilitated. In a same manner, referring to FIG. 27, second fixing pins P2 fix a second tubular body structure T2 to a second anastomosis ring R2.

As illustrated in FIG. 27, the first fixing pins P1 installed on the first anastomosis ring R1 are inserted and coupled to the second anastomosis ring R2, and the second fixing pins P2 installed on the second anastomosis ring R2 are inserted and coupled to the first anastomosis ring R1, so that the first and second anastomosis rings R1 and R2 are securely coupled to each other. The first and second tubular body structures T1 and T2 fixed to the first and second anastomosis rings R1 and R2 are connected to each other through an anastomosis by the coupling of the first and second anastomosis rings R1 and R2.

The anastomosis using rings have the following characteristics. First, the anastomosis using rings requires less time in mastering the accurate operation technique than an anastomosis using a suture. Secondly, it takes just about 2 to 3 minutes to perform the vascular anastomosis, which is significantly shorter than a vascular anastomosis using a suture. Thirdly, a monitoring result after the anastomosis using rings is not worse than the anastomosis using a suture. Fourthly, even when the diameter of a donor vessel is significantly different from that of a recipient vessel, the difference thereof can be efficiently reduced. Fifthly, the anastomosis using rings can be efficiently performed even in a limited (small) space.

SUMMARY

The present invention provides an anastomosis device that can efficiently and quickly connect tubular tissues such as blood vessels and intestines to each other through an anastomosis.

The present invention also provides an anastomosis device that can accurately and quickly perform an anastomosis.

Embodiments of the present invention provide anastomosis devices including: a first head holding a first anastomosis ring; a second head holding a second anastomosis ring; a first guide bar connected to the first head and switching a release position and a standby position to each other, wherein the first and second anastomosis rings are directed upward at the release position, and the first and second anastomosis rings face each other at the standby position, and the first guide bar includes a first rotation groove that extends in a spiral shape approximately in a longitudinal direction of the first guide bar; a second guide bar connected to the second head and switching the release position and the standby position to each other, wherein the second guide bar includes a second rotation groove that extends in a spiral shape approximately in a longitudinal direction of the second guide bar; and a rotation driver moving approximately in a parallel direction to the first and second guide bars and including a first guide protrusion and a second guide protrusion, which move along the first and second rotation grooves, respectively, wherein the first and second guide bars switch the standby position and the release position to each other according to the movements of the first and second guide protrusions along the first and second rotation grooves.

In some embodiments, the rotation driver may include a first rotation slot and a second rotation slot in which rear ends of the first and second guide bars are inserted, respectively, and the first and second guide protrusions may be installed on the first and second rotation slots to move along the first and second rotation grooves.

In other embodiments, the first guide bar may include: a first front rod and a first rear rod, which are approximately parallel to each other; and a first connecting rod that connects the first front rod to the first rear rod, the second guide bar may include: a second front rod and a second rear rod, which are approximately parallel to each other; and a second connecting rod that connects the second front rod to the second rear rod, and the anastomosis device may further include a movement driver that includes a first push slot and a second push slot in which the first and second guide bars are inserted, wherein the movement driver moves along the first and second connecting rods to switch a close position and the standby position to each other, the first and second heads come close to each other at the close position, and the first and second heads go away from each other at the standby position.

In still other embodiments, the first rear rod and the first head may have an identical first rotation axis, the first front rod may be eccentrically disposed from the first rotation axis, the second rear rod and the second head may have an identical second rotation axis, and the second front rod may be eccentrically disposed from the second rotation axis.

In even other embodiments, the first connecting rod may be inclined outward and forward when the first guide bar is disposed at the standby position, and the second connecting rod may be inclined outward and forward when the second guide bar is disposed at the standby position.

In yet other embodiments, the first rear rod may include the first rotation groove and a first movement groove that extends from the first rotation groove approximately in a longitudinal direction of the first rear rod, and the second rear rod may include the second rotation groove and a second movement groove that extends from the second rotation groove approximately in a longitudinal direction of the second rear rod.

In further embodiments, a length of the first rotation groove and the first movement groove may be approximately equal to a travelling distance of the rotation driver and the movement driver.

In still further embodiments, the movement driver may include a push bar that removes the first and second anastomosis rings from the first and second heads.

In even further embodiments, the connecting rod may be formed of an elastic material.

In yet further embodiments, the first guide bar may include: a first front rod and a first rear rod, which are approximately parallel to each other; and a first connecting rod that connects the first front rod to the first rear rod, the second guide bar may include: a second front rod and a second rear rod, which are approximately parallel to each other; and a second connecting rod that connects the second front rod to the second rear rod, and the rotation driver may include a first rotation slot and a second rotation slot in which rear ends of the first and second guide bars are inserted, respectively, wherein the first and second guide protrusions moving along the first and second rotation grooves are installed on the first and second rotation slots, and the rotation driver may further include a movement driver that moves along the first and second connecting rods to switch a close position and the standby position to each other, wherein the first and second heads come close to each other at the close position, and the first and second heads go away from each other at the standby position.

In much further embodiments, the first guide bar may include a first movement groove extending from the first rotation groove and approximately parallel to the first rotation axis, and the second guide bar may include a second movement groove extending from the second rotation groove and approximately parallel to the second rotation axis.

In still much further embodiments, the first guide bar may include a first movement groove extending from the first rotation groove, and the second guide bar may include a second movement groove extending from the second rotation groove, wherein the first movement groove includes a first front groove parallel to the first front rod, a first connecting groove parallel to the first connecting rod, and a first rear groove parallel to the first rear rod, and the second movement groove includes a second front groove parallel to the second front rod, a second connecting groove parallel to the second connecting rod, and a second rear groove parallel to the second rear rod.

BRIEF DESCRIPTION OF THE DRAWINGS

The accompanying figures are included to provide a further understanding of the present invention, and are incorporated in and constitute a part of this specification. The drawings illustrate exemplary embodiments of the present invention and, together with the description, serve to explain principles of the present invention. In the figures.

DETAILED DESCRIPTION OF THE EMBODIMENTS

Figure 1:
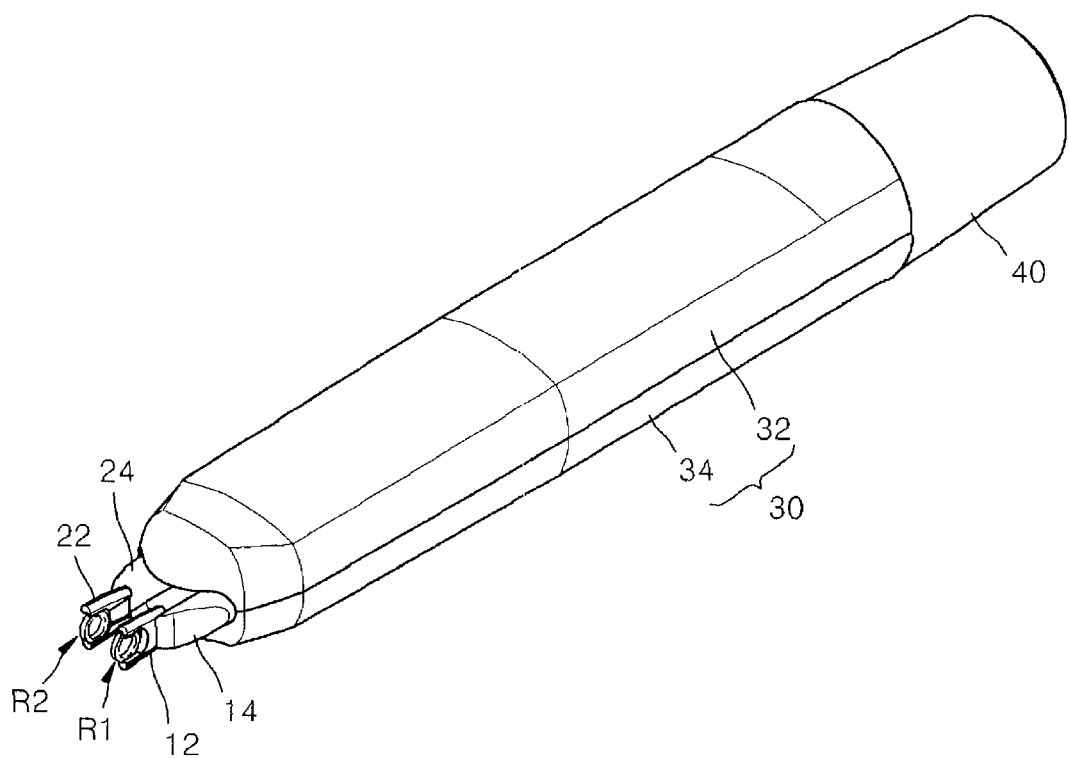
FIG. 1 is a perspective view illustrating an anastomosis device according to an embodiment of the present invention.

Preferred embodiments of the present invention will be described below in more detail with reference to FIGS. 1 through 27. The present invention may, however, be embodied in different forms and should not be constructed as limited to the embodiments set forth herein. Rather, these embodiments are provided so that this invention will be thorough and complete, and will fully convey the scope of the present invention to those skilled in the art. In the drawings, the dimensions of elements may be exaggerated for clarity of illustration.

While blood vessels are exemplified in the following embodiments, it will be understood by those skilled in the art that various changes in form and details may be made therein without departing from the spirit and scope of the present invention. In addition, the present invention may be applied to various types of minute surgeries such as a reconstruction using a free flap method, an anastomosis of a cut blood vessel, an intestinal anastomosis, treatments of a heart disease and a brain disease, a vasectomy, a prostate operation, various neurorraphies, a transplantation, and other anastomoses of tubular body structures.

Figure 2:
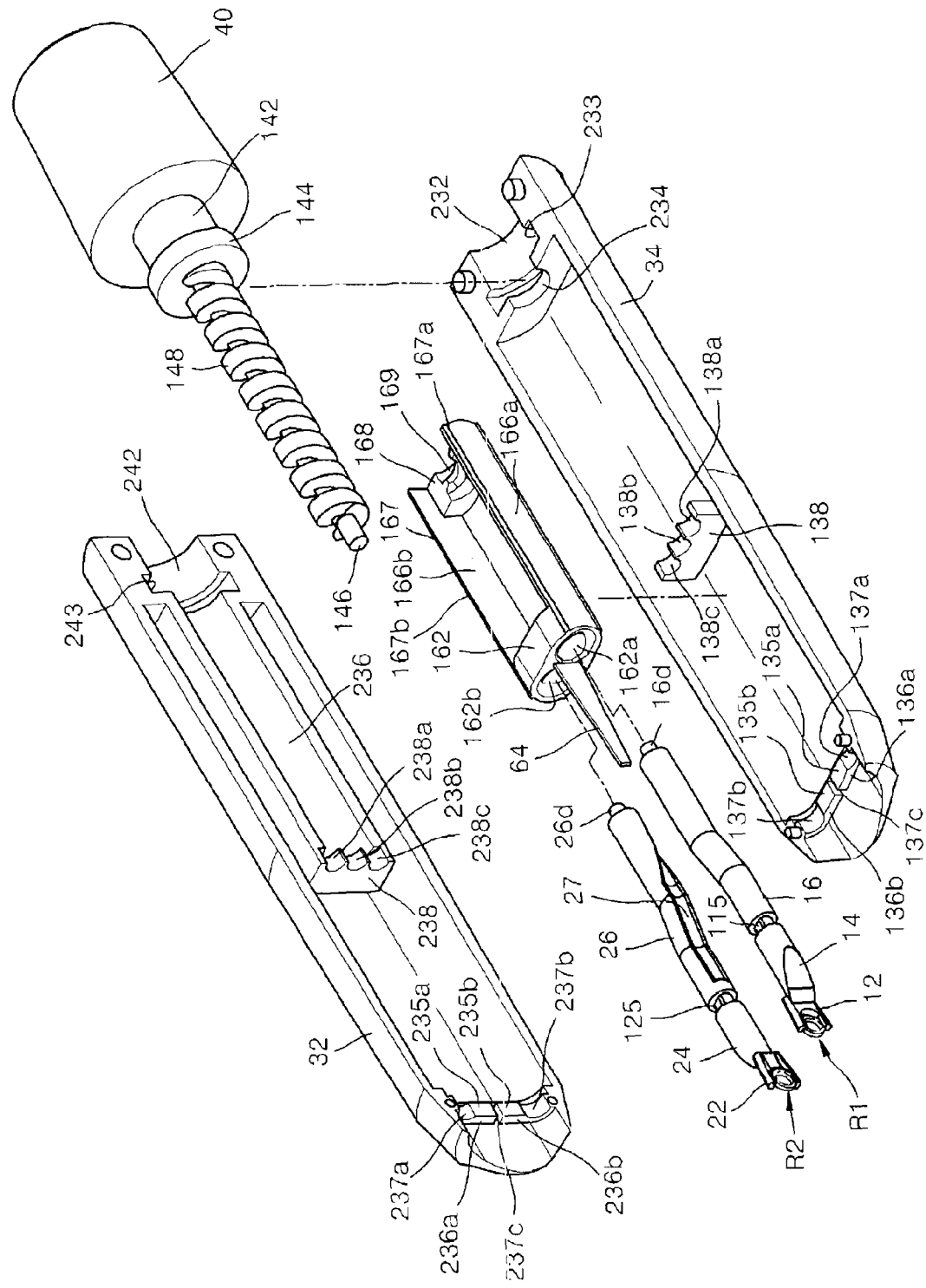
FIG. 2 is an exploded perspective view illustrating the anastomosis device of FIG. 1.

FIG. 1 is a perspective view illustrating an anastomosis device according to an embodiment of the present invention. FIG. 2 is an exploded perspective view illustrating the anastomosis device of FIG. 1. Referring to FIGS. 1 and 2, the anastomosis device includes a first holder 12 and a second holder 22, which have an approximately U shape. Each of the first and second holders 12 and 22 has an open front end. A first anastomosis ring R1 and a second anastomosis ring R2 are fixed to the first and second holders 12 and 22, respectively, through the open front ends. As described above, ends of two blood vessels to be connected through an anastomosis are fixed to the first and second anastomosis rings R1 and R2, respectively.

Referring to FIGS. 1 and 2, the first and second holders 12 and 22 are disposed such that the first and second anastomosis rings R1 and R2 face each other and are spaced apart from each other at a standby position. Then, the first and second anastomosis rings R1 and R2 come close to each other, and are connected to each other through an anastomosis.

Referring to FIG. 2, the anastomosis device further includes a first slave bar 14, a second slave bar 24, a first guide bar 16, a second guide bar 26, a first connecting bar 115, and a second connecting bar 125. The first slave bar 14 and the second slave bar 24 are connected to the first and second holders 12 and 22, respectively. The first guide bar 16 is connected to the first slave bar 14 through the first connecting bar 115. The second guide bar 26 is connected to the second slave bar 24 through the second connecting bar 125. The first and second guide bars 26 may come close to each other by a movement of a driver 160 to be described later. The first and second slave bars 14 and 24 rotate and move together with the first and second guide bars 16 and 26, so that the first and second holders 12 and 22 can rotate and move.

The anastomosis device further includes a case 30 that includes an upper case 32 and a lower case 34. The upper case 32 is disposed over the first and second guide bars 16 and 26. The lower case 34 is disposed under the first and second guide bars 16 and 26. The upper case 32 and the lower case 34 provide an inner space that is separated from the outside thereof. The first and second guide bars 16 and 26 and the driver 160 to be described later are installed in the inner space, and thus, are protected from the outside.

The upper case 32 includes a first upper front support 236a, a second upper front support 236b, and an upper rear support 238. The first upper front support 236a supports the upper portion of the first connecting bar 115, and is inserted between the first slave bar 14 and the first guide bar 16 to prevent back-and-forth movements of the first slave bar 14 and the first guide bar 16. The first upper front support 236a includes a first upper front plane 235a and a first upper front curved surface 237a, which are disposed over the first connecting bar 115.

The second upper front support 236b supports the upper portion of the second connecting bar 125, and is inserted between the second slave bar 24 and the second guide bar 26 to prevent back-and-forth movements of the second slave bar 24 and the second guide bar 26. The second upper front support 236b includes a second upper front plane 235b and a second upper front curved surface 237b, which are disposed over the second connecting bar 125.

The first and second upper front supports 236a and 236b are spaced apart from each other, and an upper push hole 237c is disposed therebetween. A push bar 64 to be described later can move forward through the upper push hole 237c.

The upper rear support 238 includes first to third upper rear support surfaces 238a, 238b, and 238c, and an upper drive shaft slot 236. The first upper rear support surface 238a supports a first rear end 16d of the first guide bar 16, and prevents the first guide bar 16 from moving rearward. The first upper rear support surface 238a is disposed over the first rear end 16d. The third upper rear support surface 238c supports a second rear end 26d of the second guide bar 26, and prevents the second guide bar 26 from moving rearward. The second upper rear support surface 238c is disposed over the second rear end 26d. The second upper rear support surface 238b supports the front end of a drive shaft 146, and is disposed over the drive shaft 146. The upper drive shaft slot 236 surrounds a thread 148 formed on an outer circumferential surface of the drive shaft 146 to protect the thread 148, and is disposed over the thread 148.

The upper case 32 includes an upper connecting shaft slot 242 having a curved shape, and an upper disk slot 243. A connecting shaft 142 to be described later is inserted in the upper connecting shaft slot 242, and rotates in the upper connecting shaft slot 242. A disk 144 to be described later is inserted in the upper disk slot 243, and rotates in the upper disk slot 243. Accordingly, a lever 40 is prevented from moving back and forth.

The lower case 34 includes a first lower front support 136a, a second lower front support 136b, and a lower rear support 138. The first lower front support 136a supports the lower portion of the first connecting bar 115, and is inserted between the first slave bar 14 and the first guide bar 16 to prevent back-and-forth movements of the first slave bar 14 and the first guide bar 16. The first lower front support 136a includes a first lower front plane 135a and a first lower front curved surface 137a, which are disposed under the first connecting bar 115.

The second lower front support 136b supports the lower portion of the second connecting bar 125, and is inserted between the second slave bar 24 and the second guide bar 26 to prevent back-and-forth movements of the second slave bar 24 and the second guide bar 26. The second lower front support 136b includes a second lower front plane 135b and a second lower front curved surface 137b, which are disposed under the second connecting bar 125.

The first and second lower front supports 136a and 136b are spaced apart from each other, and a lower push hole 137c is disposed therebetween. The push bar 64 to be described later can move forward through the lower push hole 137c.

The lower rear support 138 includes first to third lower rear support surfaces 138a, 138b, and 138c. The first lower rear support surface 138a supports the first rear end 16d of the first guide bar 16, and prevents the first guide bar 16 from moving rearward. The first lower rear support surface 138a is disposed under the first rear end 16d. The third lower rear support surface 138c supports the second rear end 26d of the second guide bar 26, and prevents the second guide bar 26 from moving rearward. The second lower rear support surface 138c is disposed under the second rear end 26d. The second lower rear support surface 138b supports the front end of the drive shaft 146, and is disposed under the drive shaft 146.

Figure 3:
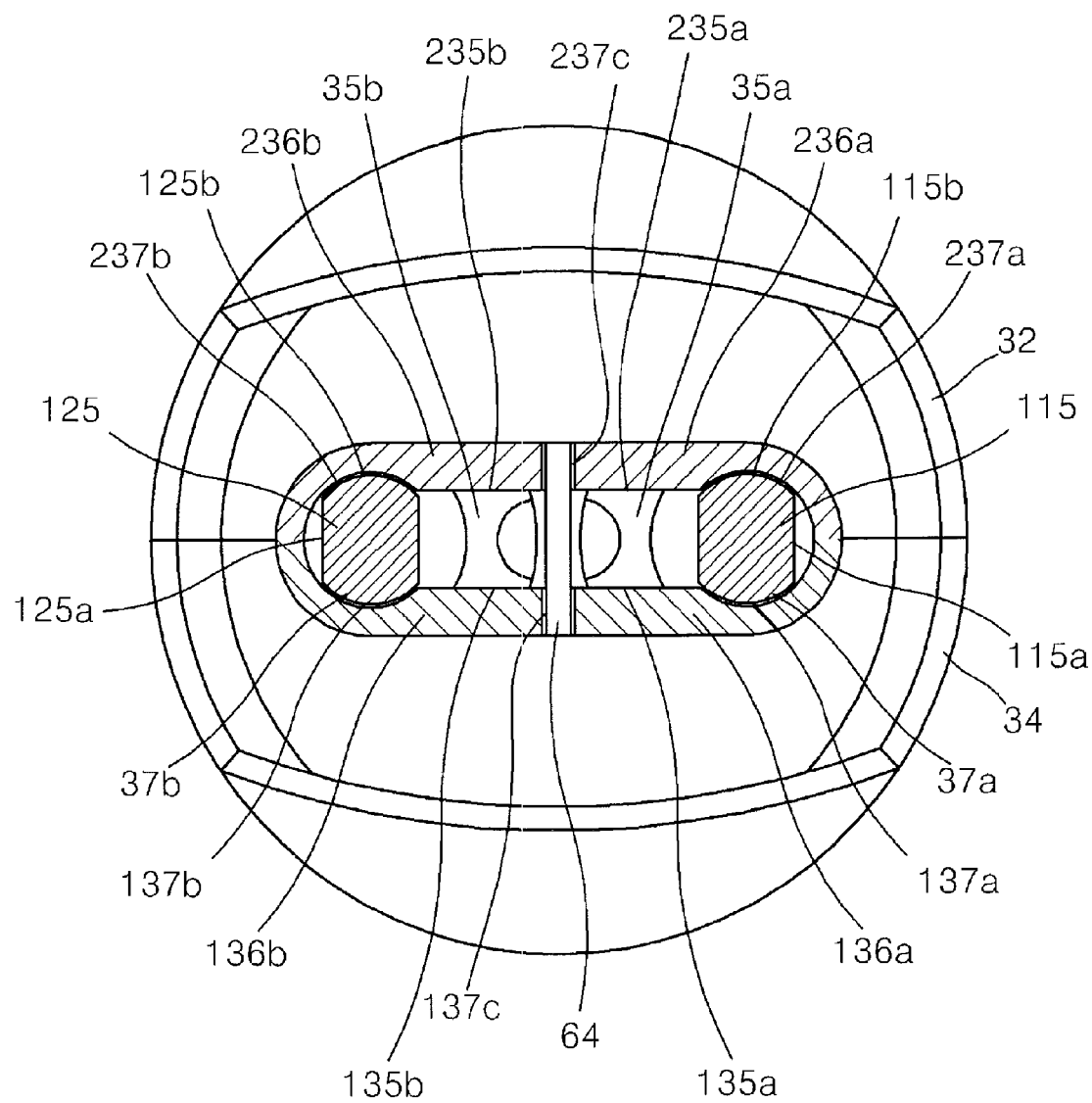
FIGS. 3 and 4 are cross-sectional views illustrating first and second connecting bars rotating and moving between first and second upper front supports and first and second lower front supports according to an embodiment of the present invention.
Figure 4:
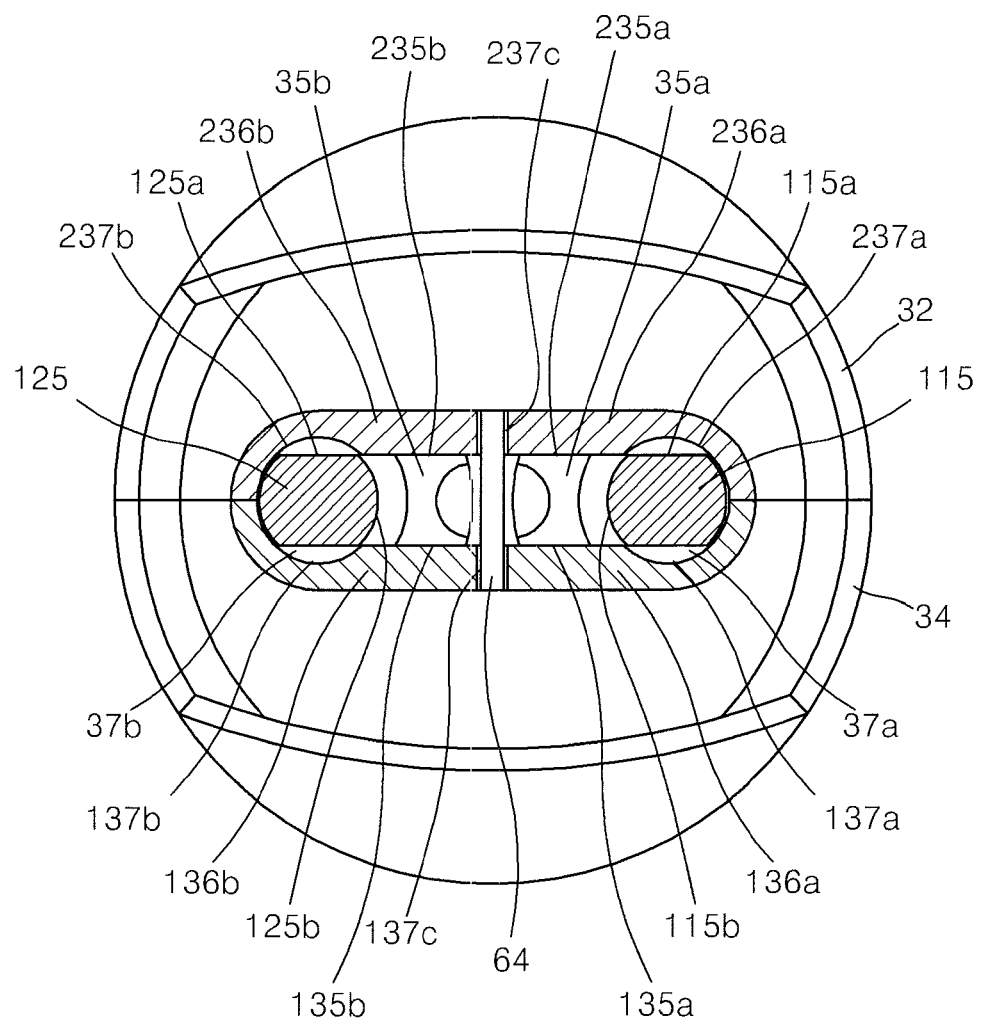

FIGS. 3 and 4 are cross-sectional views illustrating first and second connecting bars rotating and moving between first and second upper front supports and first and second lower front supports according to an embodiment of the present invention. Referring to FIGS. 3 and 4, the first lower front plane 135a and the first lower front curved surface 137a are disposed under the first connecting bar 115, and the first upper front plane 235a and the first upper front curved surface 237a are disposed over the first connecting bar 115.

The first lower front plane 135a and the first upper front plane 235a are spaced apart from each other, and a first movement space 35a is formed therebetween. The first lower front curved surface 137a and the first upper front curved surface 237a are spaced apart from each other, and a first rotation space 37a is formed therebetween. As illustrated in FIGS. 3 and 4, the first rotation space 37a has a circular cross-section with a predetermined diameter, and the diameter of the first rotation space 37a is greater than the height of the first movement space 35a.

As illustrated in FIGS. 3 and 4, the first connecting bar 115 includes first movement surfaces 115a that are flat and parallel to each other, and first rotation surfaces 115b that are curved and connect the first movement surfaces 115a to each other. The first rotation surfaces 115b define a predetermined diameter about the center of the first connecting bar 115. The diameter defined by the first rotation surfaces 115b is greater than the height of the first movement space 35a and is smaller than the diameter of the first rotation space 37a. A distance between the first movement surfaces 115a is smaller than the height of the first movement space 35a.

Referring to FIGS. 3 and 4, rotations and movements of the first connecting bar 115 will now be described. The first connecting bar 115 rotates only within the first rotation space 37a, and moves to the second connecting bar 125 only within the first movement space 35a. In the state as illustrated in FIG. 3, since the diameter defined by the first rotation surfaces 115b is greater than the height of the first movement space 35a, the first connecting bar 115 cannot move to the first movement space 35a, and the first connecting bar 115 can just rotate within the first rotation space 37a. As illustrated in FIG. 4, when the first connecting bar 115 rotates within the first rotation space 37a such that the first movement surfaces 115a are parallel to the first lower front plane 135a and the first upper front plane 235a, since the distance between the first movement surfaces 115a is smaller than the height of the first movement space 35a, the first connecting bar 115 can move along the first movement space 35a. At this point, since the first movement surfaces 115a moves along the first lower front plane 135a and the first upper front plane 235a, the first connecting bar 115 cannot rotate within the first movement space 35a.

Referring to FIGS. 3 and 4, the second lower front plane 135b and the second lower front curved surface 137b are disposed under the second connecting bar 125, and the second upper front plane 235b and the second upper front curved surface 237b are disposed over the second connecting bar 125.

At this point, the second lower front plane 135b and the second upper front plane 235b are spaced apart from each other, and a second movement space 35b is formed therebetween. The second lower front curved surface 137b and the second upper front curved surface 237b are spaced apart from each other, and a second rotation space 37b is formed therebetween. As illustrated in FIGS. 3 and 4, the second rotation space 37b has a circular cross-section with a predetermined diameter, and the diameter of the first rotation space 37a is greater than the height of the second movement space 35b.

As illustrated in FIGS. 3 and 4, the second connecting bar 125 includes second movement surfaces 125a that are flat and parallel to each other, and second rotation surfaces 125b that are curved and connect the second movement surfaces 125a to each other. The second rotation surfaces 125b define a diameter about the center of the second connecting bar 125. The diameter defined by the second rotation surfaces 115b is greater than the height of the second movement space 35b and is smaller than the diameter of the second rotation space 37b. A distance between the second movement surfaces 125a is smaller than the height of the second movement space 35b.

Referring to FIGS. 3 and 4, rotations and movements of the second connecting bar 125 will now be described. The second connecting bar 125 rotates only within the second rotation space 37b, and moves to the first connecting bar 115 only within the second movement space 35b. In the state as illustrated in FIG. 3, since the diameter defined by the second rotation surfaces 125b is greater than the height of the second movement space 35b, the second connecting bar 125 cannot move to the second movement space 35b, and the second connecting bar 125 can just rotate within the second rotation space 37b. As illustrated in FIG. 4, when the second connecting bar 125 rotates within the second rotation space 37a such that the second movement surfaces 125a are parallel to the second lower front plane 135b and the second upper front plane 235b, since the distance between the second movement surfaces 125a is smaller than the height of the second movement space 35b, the second connecting bar 125 can move along the first movement space 35b. At this point, since the second movement surfaces 125a move along the second lower front plane 135b and the second upper front plane 235b, the second connecting bar 125 cannot rotate within the second movement space 35b.

The lower case 34 includes a lower connecting shaft slot 232 having a curved shape, a lower disk slot 233, and a lower drive shaft slot 234. The connecting shaft 142 to be described later is inserted in the lower connecting shaft slot 232, and rotates in the lower connecting shaft slot 232. The disk 144 to be described later is inserted in the lower disk slot 233, and rotates in the lower disk slot 233. The drive shaft 146 to be described later is inserted in the lower drive shaft slot 234, and rotates therein.

Referring to FIG. 2, the anastomosis device further includes the lever 40, the disk 144, and the drive shaft 146. The lever 40 is cylindrical, and is rotated to move the driver 160 along the longitudinal direction of the case 30. The drive shaft 146 has the thread 148 on the outer circumferential surface thereof, and the thread 148 engages with a thread of a moving body 168 to be described. The drive shaft 146 is connected to the lever 40 through the connecting shaft 142 and the disk 144. When the lever 40 rotates, the drive shaft 146 rotates together with the connecting shaft 142 and the disk 144. Thus, the moving body 168 (or the driver 160) moves along the longitudinal direction of the case 30. As described above, the connecting shaft 142 rotates within the lower connecting shaft slot 242 and the upper connecting shaft slot 242, and the disk 144 rotates within the lower disk slot 233 and the upper disk slot 243. At this point, the lower disk slot 233 and the upper disk slot 243 prevent a back-and-forth movement of the disk 144, and thus, the drive shaft 146 is maintained at a set position thereof.

Referring to FIG. 2, the anastomosis device includes the driver 160. The driver 160 includes a first drive slot 162a and a second drive slot 162b. The rear ends of the first and second guide bars 16 and 26 are inserted in the first and second drive slots 162a and 162b. The driver 160 moves forward or backward in the longitudinal direction of the case 30 by an operation of the lever 40, and the first and second guide bars 16 and 26 rotate and move accordingly.

Figure 5:
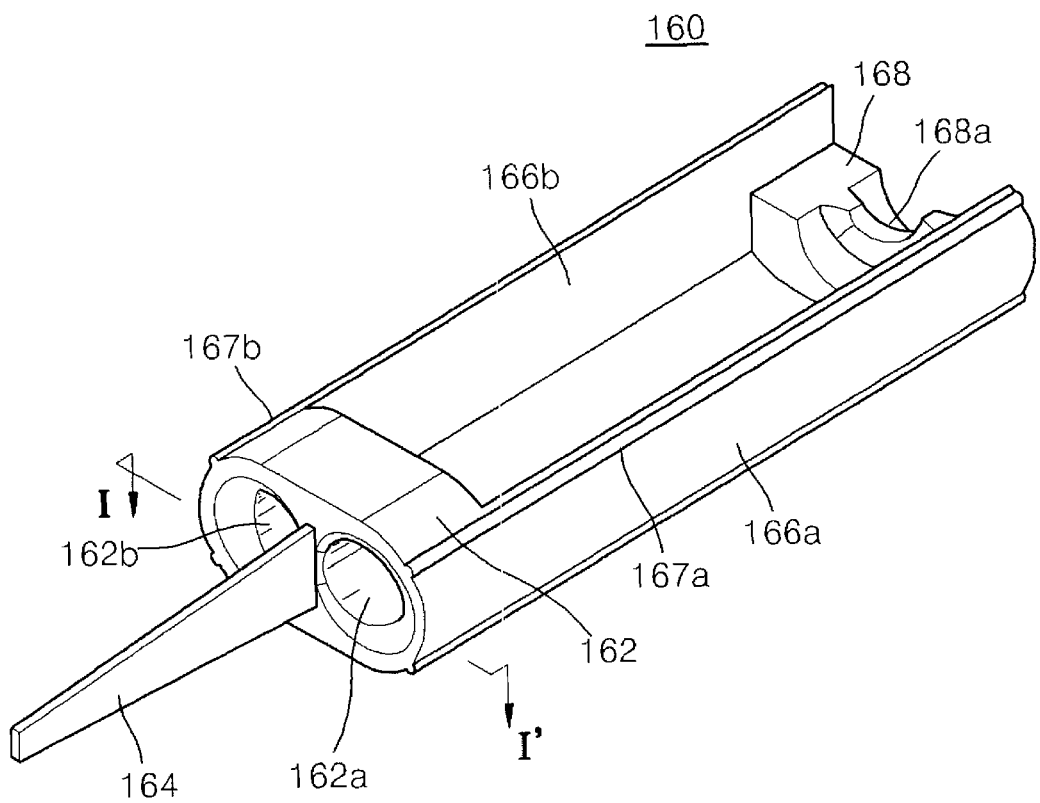
FIG. 5 is a perspective view illustrating a driver of FIG. 2.
Figure 6:
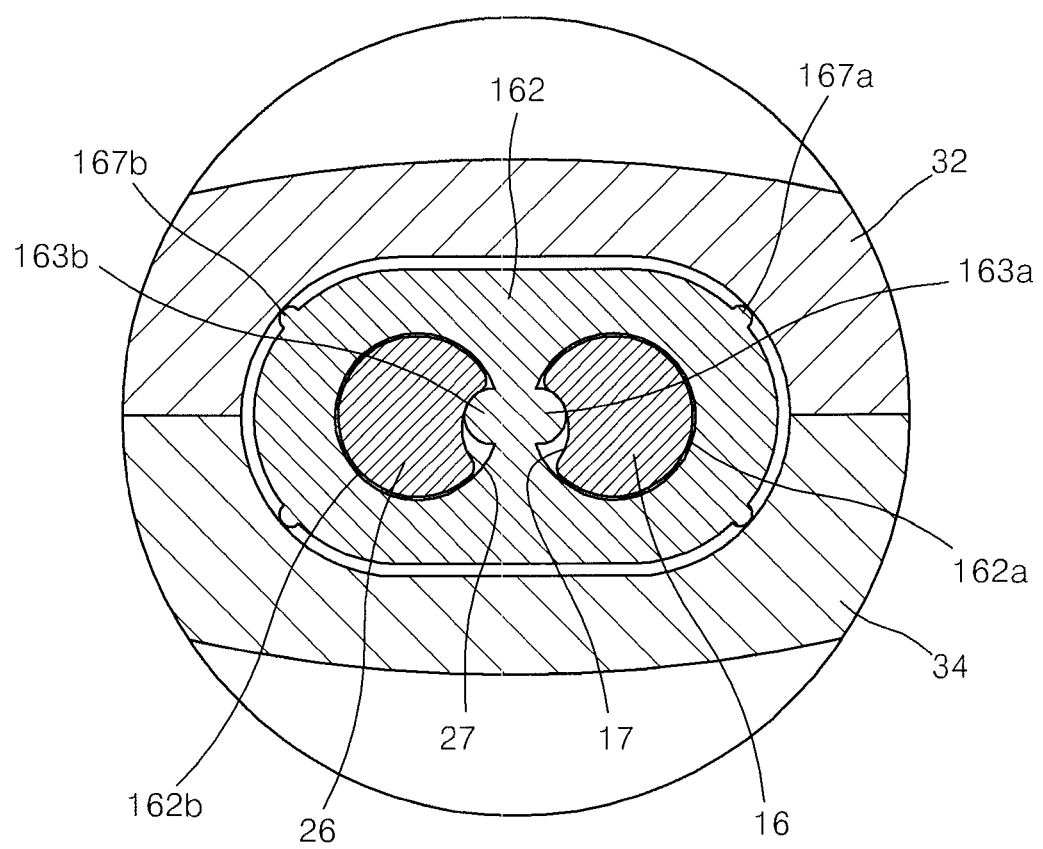
FIG. 6 is a cross-sectional view illustrating the driver of FIG. 2.
Figure 7:
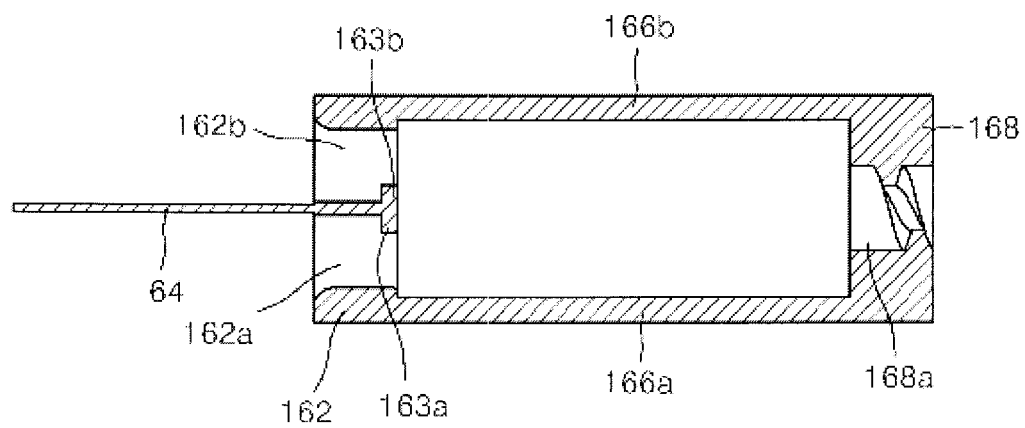
FIG. 7 is a cross-sectional view taken along line I-I' of FIG. 5.

FIG. 5 is a perspective view illustrating the driver of FIG. 2. FIG. 6 is a cross-sectional view illustrating the driver of FIG. 2. FIG. 7 is a cross-sectional view taken along line I-I' of FIG. 5. Referring to FIG. 5, the driver 160 includes a driving body 162, the push bar 64, connecting plates 166a and 166b, and the moving body 168.

The driving body 162 has an oval cross-section that corresponds to the inner space of the case 30. The driving body 162 includes the first and second drive slots 162a and 162b, which extend in the longitudinal direction of the case 30. The rear ends of the first and second guide bars 16 and 26 are inserted in the first and second drive slots 162a and 162b, respectively. Referring to FIGS. 6 and 7, each of inner surfaces of the first and second drive slots 162a and 162b has a straight line part that extends approximately in the longitudinal direction of the case 30, and an inclination part that is inclined outward at an end of the straight line part. Accordingly, a diameter of the inclination part is greater than that of the straight line part. The first and second guide bars 16 and 26 are inserted in the first and second drive slots 162*a* and 162*b*, and the inner surfaces of the first and second drive slots 162*a* and 162*b* displace the first and second guide bars 16 and 26, which will be described later. At this point, the inclination parts prevent quick displacements of the first and second guide bars 16 and 26.

A first guide protrusion 163*a* and a second guide protrusion 163*b* are disposed at positions adjacent to each other on the inner surfaces of the first and second drive slots 162*a* and 162*b*. The first guide protrusion 163*a* is inserted in first guide grooves 17*a* and 17*b* to be described later, and moves along the first guide grooves 17*a* and 17*b*. The first guide bar 16 is rotated by a movement of the first guide protrusion 163*a*. The second guide protrusion 163*b* is inserted in second guide grooves 27*a* and 27*b* to be described later, and moves along the second guide grooves 27*a* and 27*b*. The second guide bar 26 is rotated by a movement of the second guide protrusion 163*b*. This will be described later in detail.

As illustrated in FIG. 5, the push bar 64 is disposed at the front side of the driving body 162 between the first and second drive slots 162*a* and 162*b*. The push bar 64 has a vertically standing plate shape and decreases in cross-section forward. When the first and second anastomosis rings R1 and R2 are coupled to each other and are fixed between the first and second holders 12 and 22, the front end of the push bar 64 removes the first and second anastomosis rings R1 and R2 from the first and second holders 12 and 22. Alternatively, the push bar 64 may be provided in the form of a pin.

The moving body 168 is disposed at the rear side of the driving body 162 and includes a through hole 168*a* extending approximately in a moving direction of the driver 160. The moving body 168 includes the thread on an inner circumferential surface of the through hole 168*a*, and the thread of the moving body 168 engages with the thread 148 of the drive shaft 146. Thus, according to a rotation of the drive shaft 146, the moving body 168 moves along the longitudinal direction of the case 30. The connecting plates 166*a* and 166*b* extend rearward from side portions of the driving body 162, and connect to the moving body 168 to move together with the moving body 168.

The driver 160 includes first guide rails 167*a* and second guide rails 167*b*, which are fixed to the driving body 162 and side surfaces of the connecting plates 166*a* and 166*b*. When the driver 160 moves, the first and second guide rails 167*a* and 167*b* are in sliding contact with the inner surfaces of the upper case 32 and the lower case 34. Thus, a contact area between the driver 160 and the upper case 32 and a contact area between the driver 160 and the lower case 34 decrease. In addition, when the driver 160 moves, frictional force between the driver 160 and the upper case 32 and frictional force between the driver 160 and the lower case 34 are minimized.

Figure 8:
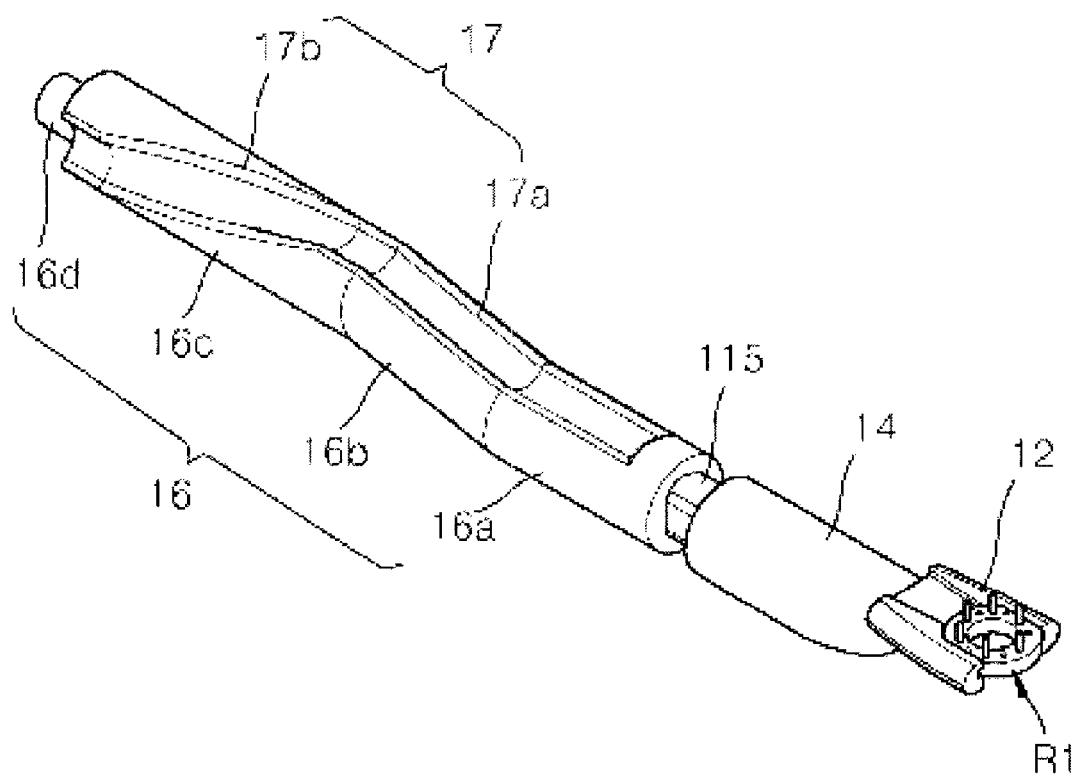
FIG. 8 is a perspective view illustrating a first holder, a first connecting bar, and a first guide bar as shown in FIG. 2.

FIG. 8 is a perspective view illustrating the first holder, the first connecting bar, and the first guide bar as shown in FIG. 2. As described above, the first anastomosis ring R1 is fixed to the first holder 12 through the open front end of the first holder 12, and the first holder 12 is connected to the front end of the first slave bar 14. The first connecting bar 115 connects the first slave bar 14 to the first guide bar 16 and is smaller in diameter than the first slave bar 14 and the first guide bar 16. Thus, a stepped part is formed between the first slave bar 14 and the first guide bar 16, and the first upper front support 236*a* is inserted between the first slave bar 14 and the first guide bar 16 to prevent back-and-forth movements of the first slave bar 14 and the first guide bar 16.

The first guide bar 16 includes a first front rod 16*a*, a first rear rod 16*c*, a first connecting rod 16*b* connecting the first front rod 16*a* to the first rear rod 16*c*, and the first rear end 16*d* connected to the rear end of the first rear rod 16*c*. The first front rod 16*a* is disposed eccentrically from a rotation axis of the first rear rod 16*c*. An eccentric direction of the first front rod 16*a* is opposite to the direction that the surface of the first anastomosis ring R1 provided with the fixing pins P1 is exposed. Thus, the first connecting rod 16*b* extends obliquely. The first rear end 16*d* is smaller in diameter than the first rear rod 16*c*. The first upper rear support surface 238*a* supports the first rear end 16*d* to prevent the first guide bar 16 from moving rearward.

The first guide bar 16 includes a first guide groove 17 that includes a first movement groove (also denoted by 17*a*) and a first rotation groove (also denoted by 17*b*). The first movement groove 17*a* extends approximately in the longitudinal directions of the first front rod 16*a* and the first connecting rod 16*b*. The first rotation groove 17*b* extends from the rear end of the first movement groove 17*a* and has a spiral shape that extends in the longitudinal direction of the first rear rod 16*c* as a whole. As illustrated in FIG. 8, the first rotation groove 17*b* spirals counterclockwise to the front side of the first rear rod 16*c*, and has a predetermined angle θ about the rotation axis (or central axis) of the first rear rod 16*c*, from the rear end of the first rotation groove 17*b* to the front end thereof.

Figure 9:
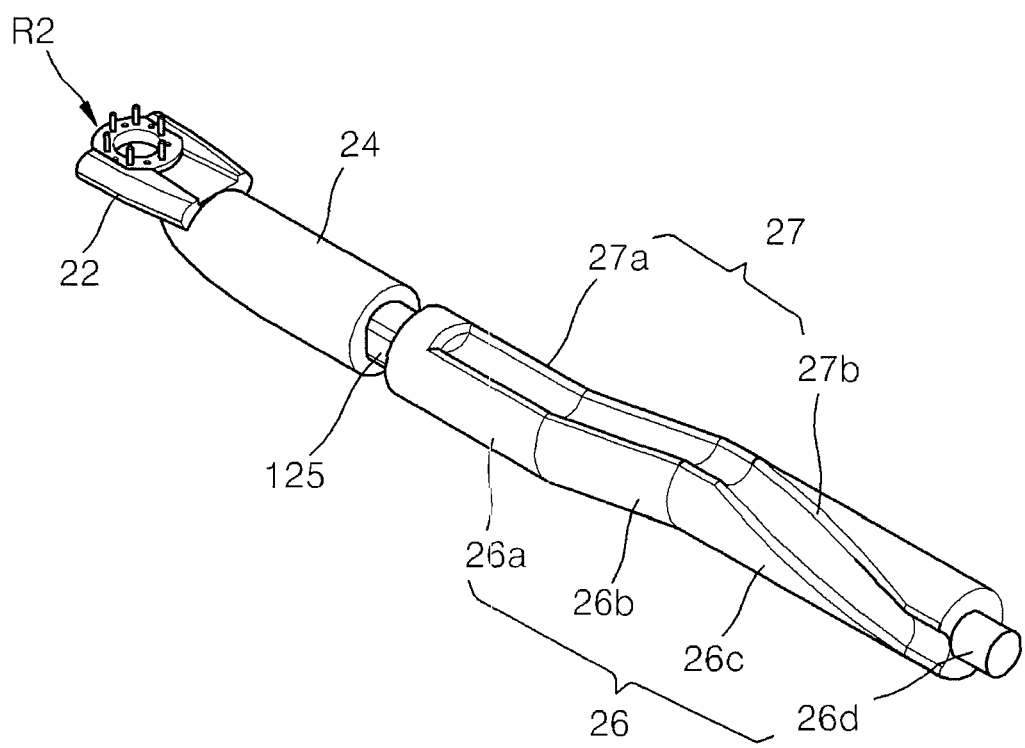
FIG. 9 is a perspective view illustrating a second holder, a second connecting bar, and a second guide bar as shown in FIG. 2.

FIG. 9 is a perspective view illustrating the second holder, the second connecting bar, and the second guide bar as shown in FIG. 2. As described above, the second anastomosis ring R2 is fixed to the second holder 22 through the open front end of the second holder 22, and the second holder 22 is connected to the front end of the second slave bar 24. The second connecting bar 125 connects the second slave bar 24 to the second guide bar 26 and is smaller in diameter than the second slave bar 24 and the second guide bar 26. Thus, a stepped part is formed between the second slave bar 24 and the second guide bar 26, and the second upper front support 236*b* is inserted between the second slave bar 24 and the second guide bar 26 to prevent back-and-forth movements of the second slave bar 24 and the second guide bar 26.

The second guide bar 26 includes a second front rod 26*a*, a second rear rod 26*c*, a second connecting rod 26*b* connecting the second front rod 26*a* to the second rear rod 26*c*, and the second rear end 26*d* connected to the rear end of the second rear rod 26*c*. The second front rod 26*a* is disposed eccentrically from a rotation axis of the second rear rod 26*c*. An eccentric direction of the second front rod 26*a* is opposite to the direction that the surface of the second anastomosis ring R2 provided with the fixing pins P2 is exposed. Thus, the second connecting rod 26*b* extends obliquely. The second rear end 26*d* is smaller in diameter than the second rear rod 26*c*. The third upper rear support surface 238*c* supports the second rear end 26*d* to prevent the second guide bar 26 from moving rearward.

The second guide bar 26 includes a second guide groove 27 that includes a second movement groove (also denoted by 27*a*) and a second rotation groove (also denoted by 27*b*). The second movement groove 27*a* extends approximately in the longitudinal directions of the second front rod 26*a* and the second connecting rod 26*b*. The second rotation groove 27*b* extends from the rear end of the second movement groove 27*a* and has a spiral shape that extends in the longitudinal direction of the second rear rod 26*c* as a whole. As illustrated in FIG. 9, the second rotation groove 27*b* spirals clockwise to the front side of the second rear rod 26*c*, and has a predetermined angle θ about the rotation axis (or central axis) of the second rear rod 26c, from the rear end of the second rotation groove 27b to the front end thereof.

Figure 10:
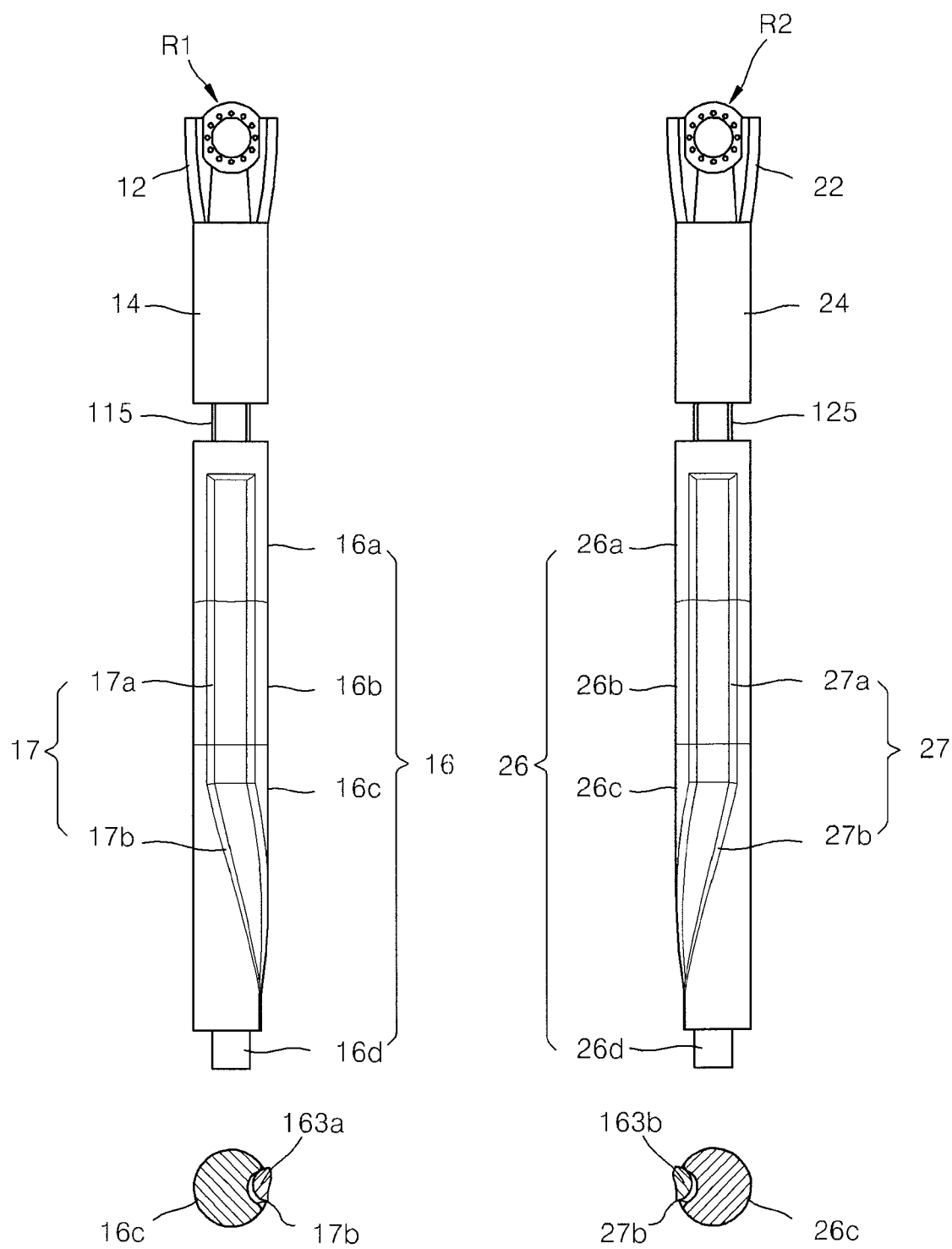
FIGS. 10 and 11 are plan views illustrating rotations of first and second guide bars according to movements of first and second guide protrusions along first and second rotation grooves according to an embodiment of the present invention.
Figure 11:
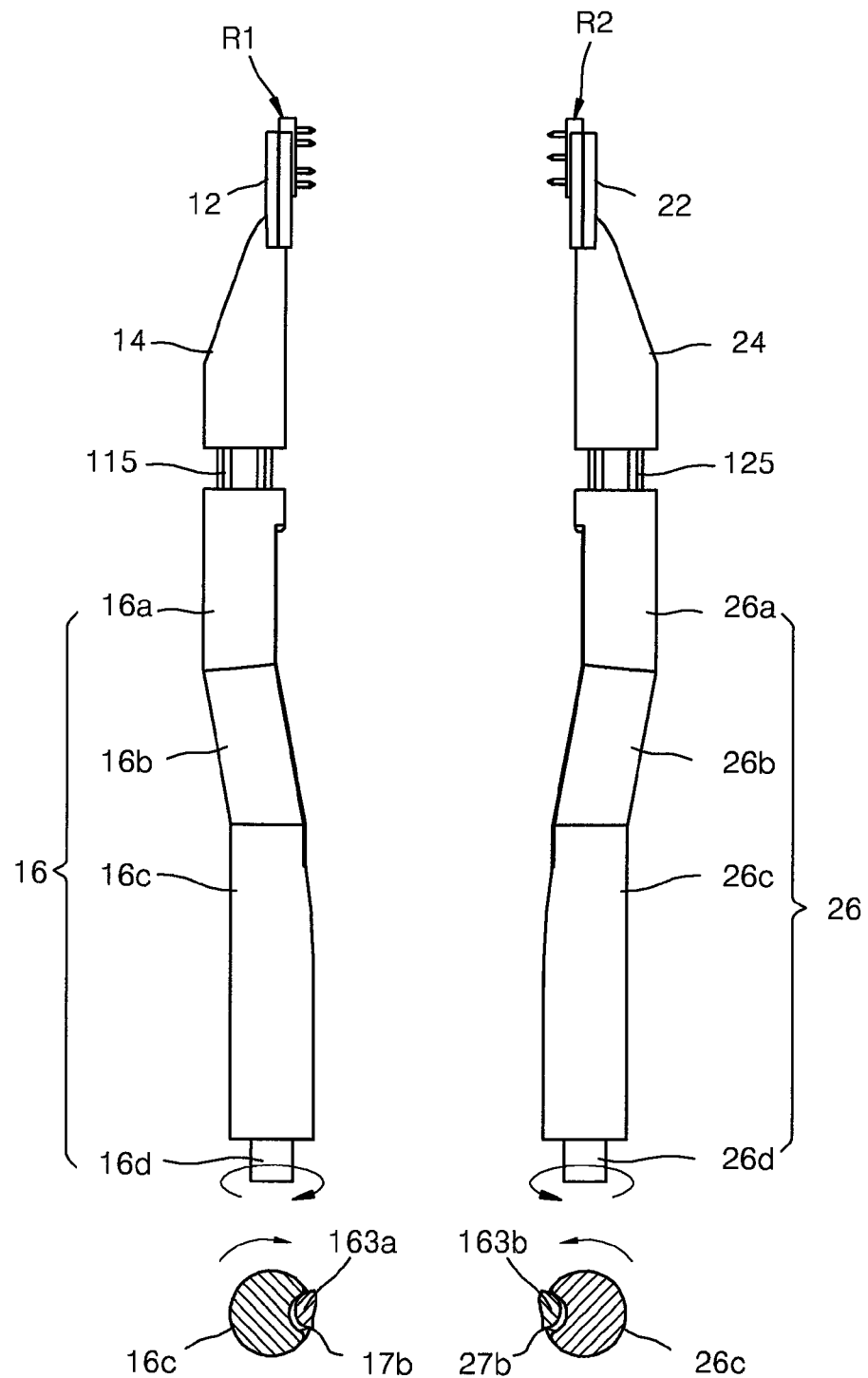

FIGS. 10 and 11 are plan views illustrating rotations of first and second guide bars according to movements of first and second guide protrusions along first and second rotation grooves according to an embodiment of the present invention. Hereinafter, rotations of first and second guide bars will now be described with reference to FIGS. 10 and 11.

As described above, the first guide protrusion 163a is inserted in the first movement groove 17a and the first rotation groove 17b, and moves along the first movement groove 17a and the first rotation groove 17b according to a back-and-forth movement of the driver 160. The second guide protrusion 163b is inserted in the second movement groove 27a and the second rotation groove 27b, and moves along the second movement groove 27a and the second rotation groove 27b according to a back-and-forth movement of the driver 160.

Referring to FIG. 10, the first and second holders 12 and 22 are approximately parallel to a ground or are slightly inclined from the ground (at the release position). At this point, the first and second anastomosis rings R1 and R2 are connected to the first and second holders 12 and 22, respectively, through the open ends of the first and second holders 12 and 22. When the first and second holders 12 and 22 are disposed at the release position, the first and second guide protrusions 163b and 163b are disposed at the rear ends of the first and second rotation grooves 17b and 27b, respectively.

Hereinafter, when the lever 40 is operated to rotate the drive shaft 146, the driver 160 moves forward. As the driver 160 moves forward, the first and second guide protrusions 163a and 163b move along the first and second rotation grooves 17b and 27b. At this point, the first rear rod 16c rotates clockwise, and the second rear rod 26c rotates counterclockwise, as illustrated in FIG. 11. This is because the first and second guide protrusions 163a and 163b confine the positions of the first and second rotation grooves 17b and 27b.

When the first and second guide protrusions 163a and 163b arrive at the front ends of the first and second rotation grooves 17b and 27b, the first and second rear rods 16c and 26c rotate by the above-described angle θ, and the first and second holders 12 and 22 move from the release position to the standby position.

Figure 12:
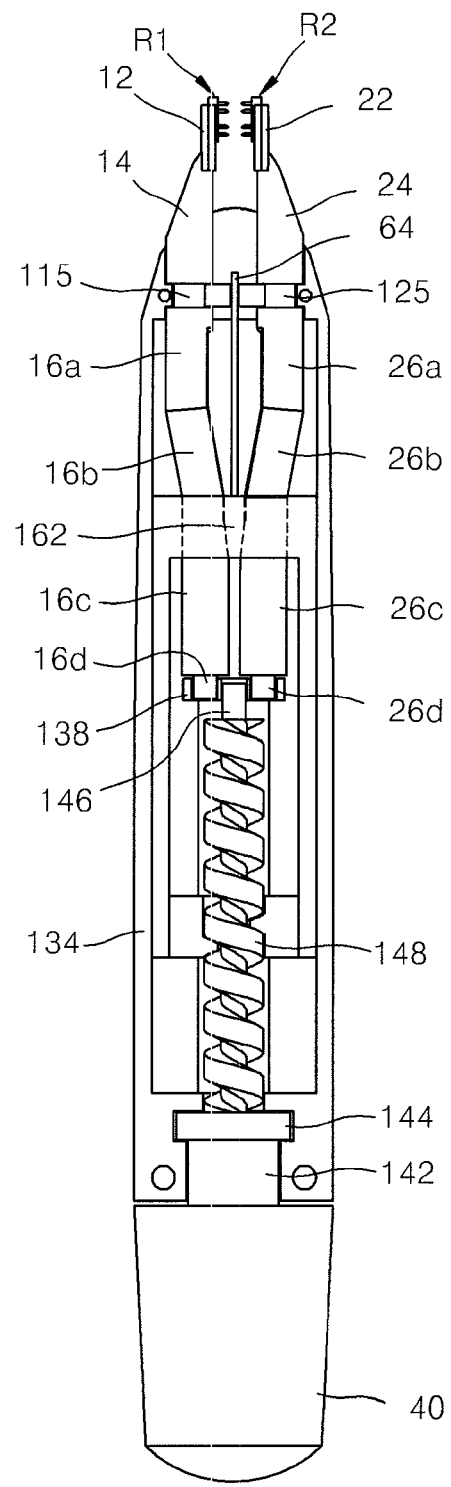
FIGS. 12 and 13 are plan views illustrating movements of first and second guide bars according to movements of first and second guide protrusions along first and second movement grooves according to an embodiment of the present invention.
Figure 13:
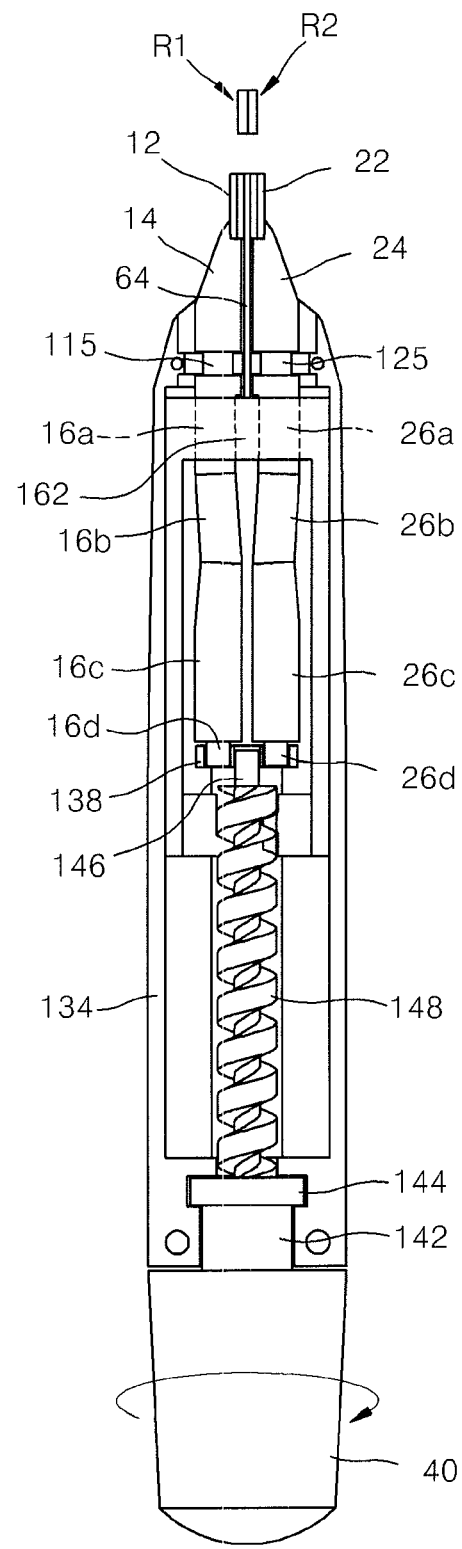

FIGS. 12 and 13 are plan views illustrating movements of first and second guide bars according to movements of first and second guide protrusions along first and second movement grooves according to an embodiment of the present invention. Hereinafter, rotations of the first and second front rods 16a and 26a will now be described with reference to FIGS. 12 and 13.

As described above, when the first and second guide protrusions 163a and 163b arrive at the front ends of the first and second rotation grooves 17b and 27b, the first and second holders 12 and 22 move from the release position to the standby position. In addition, as illustrated in FIG. 12, the first and second front rods 16a and 26a spread wider than the first and second rear rods 16c and 26c, and the first and second connecting rods 16b and 26b extend forward and inclined outward. At this point, the front ends of the first and second drive slots 162a and 162b of the driver 160 are disposed at the front ends of the first and second rear rods 16c and 26c.

As described above, when an operator operates the lever 40 to rotate the drive shaft 146, the driver 160 moves forward. At this point, the inner surfaces of the first and second drive slots 162a and 162b sequentially press the outer surfaces of the first and second connecting rods 16b and 26b, and the outer surfaces of the first and second front rods 16a and 26a. Thus, as illustrated in FIG. 13, the front ends of the first and second front rods 16a and 26a come close to each other. At this point, the first and second connecting rods 16b and 26b are bent by the pressing of the first and second drive slots 162a and 162b, and may be formed of polymer (for example, PE-based material) having small elasticity, or a metal. If the first and second connecting rods 16b and 26b have elasticity, when the driver 160 returns its original position, the front ends of the first and second front rods 16a and 26a also return their original positions. Each of the first and second guide bars 16 and 26 may be provided in the form of a single body, and be formed of polymer having small elasticity or a metal, as described above.

The front ends of the first and second slave bars 14 and 24 come close to each other, and the first and second holders 12 and 22 come close to each other accordingly (close position). Accordingly, the first and second anastomosis rings R1 and R2 fixed to the first and second holders 12 and 22 come close to each other and couple to each other.

After the first and second anastomosis rings R1 and R2 are coupled to each other, the front end of the push bar 64 is inserted between the first and second holders 12 and 22, and the first and second anastomosis rings R1 and R2 are removed from the first and second holders 12 and 22.

Figure 14:
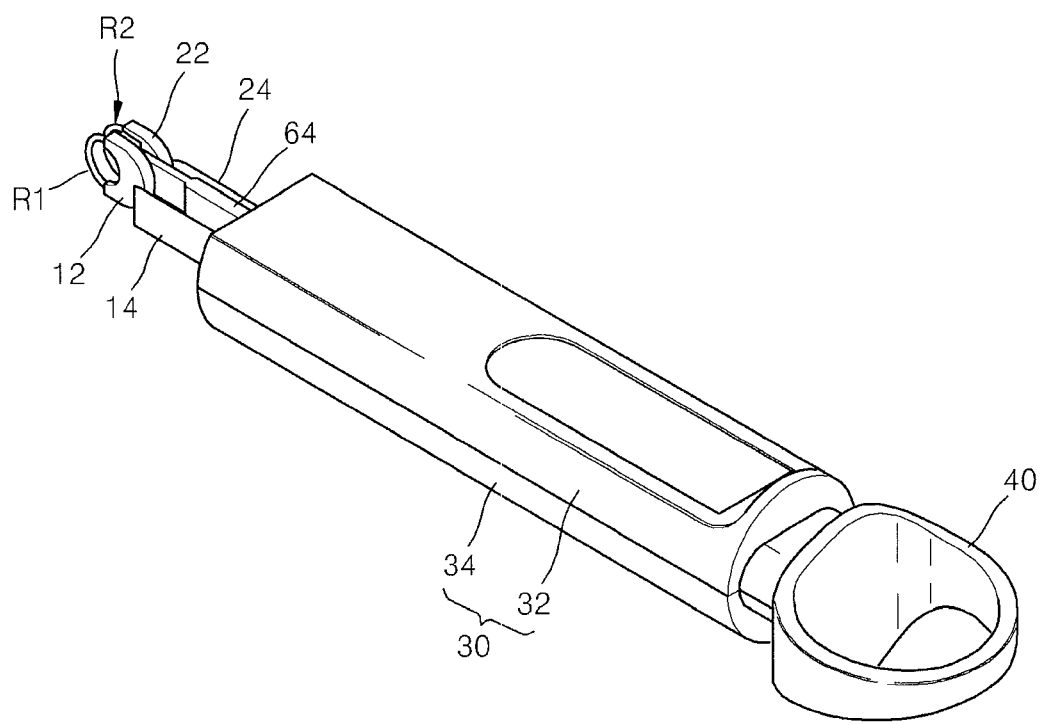
FIG. 14 is a perspective view illustrating an anastomosis device according to an embodiment of the present invention.
Figure 15:
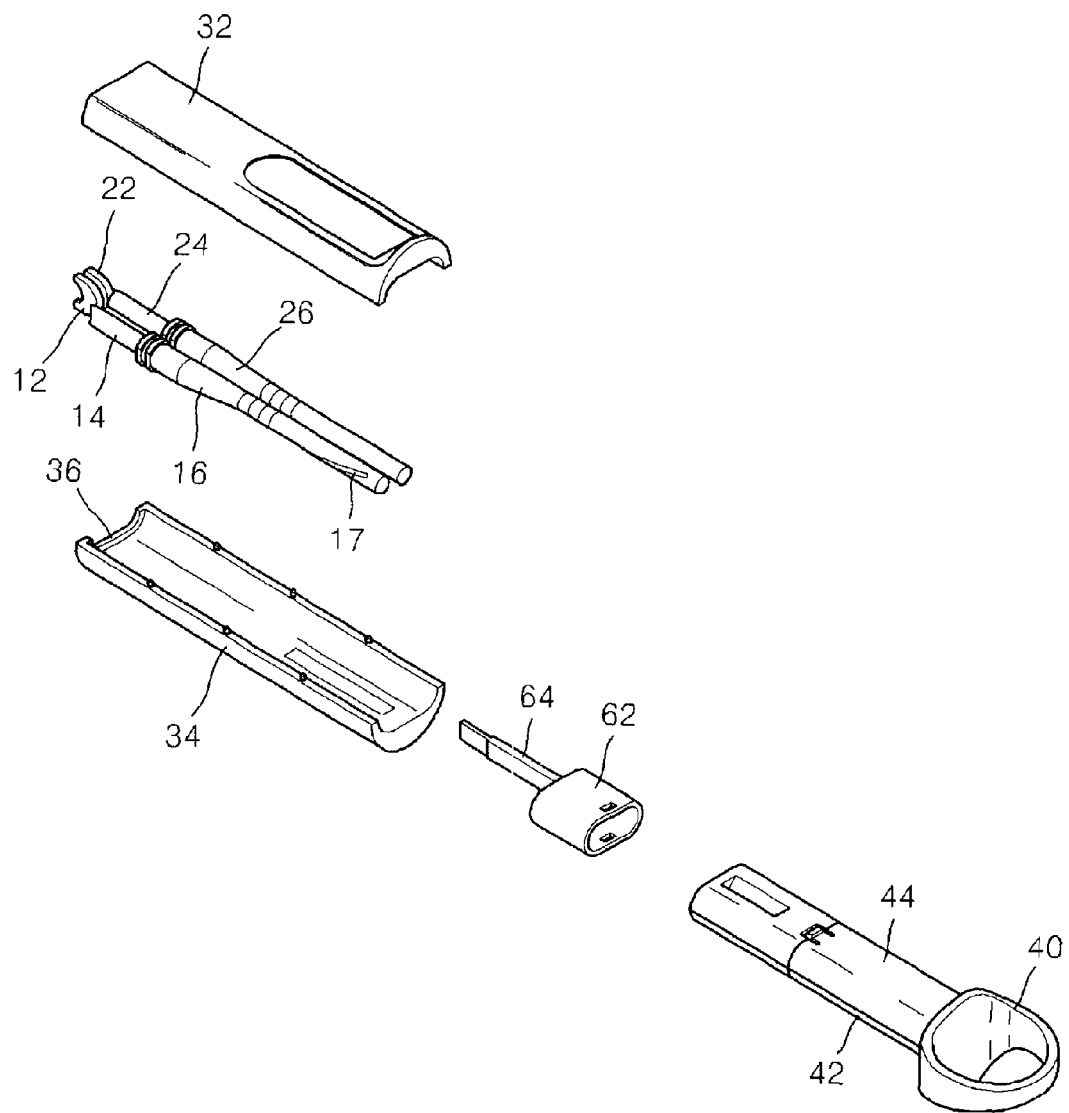
FIG. 15 is an exploded perspective view illustrating the anastomosis device of FIG. 14.

FIG. 14 is a perspective view illustrating an anastomosis device according to an embodiment of the present invention. FIG. 15 is an exploded perspective view illustrating the anastomosis device of FIG. 14. Referring to FIGS. 14 and 15, the anastomosis device includes the first holder 12 and the second holder 22, which have an approximately U shape. The first and second anastomosis rings R1 and R2 are fixed to the first and second holders 12 and 22, respectively, through the open front ends of the first and second holders 12 and 22. The ends of blood vessels to be connected to each other through an anastomosis are fixed to the first and second anastomosis rings R1 and R2, respectively. Referring to FIGS. 14 and 15, the first and second holders 12 and 22 are disposed such that the first and second anastomosis rings R1 and R2 face each other, and are spaced apart from each other at the standby position. Then, the first and second holders 12 and 22 come close to each other, and the first and second anastomosis rings R1 and R2 are connected to each other to perform an anastomosis on the blood vessels. Since the shapes and coupling methods of anastomosis rings are well known in the art, a description thereof will be omitted.

The anastomosis device includes the first slave bar 14, the second slave bar 24, the first guide bar 16, and the second guide bar 26. The first slave bar 14 and the second slave bar 24 are connected to the first and second holders 12 and 22, respectively. The first guide bar 16 and the second guide bar 26 are connected to the first and second slave bars 14 and 24, respectively. The first and second guide bars 16 and 26 are rotated by rotation drivers 42 and 44 to be described later and come close to each other by a movement driver 62 to be described later. The first and second slave bars 14 and 24 rotate and move together with the first and second guide bars 26, so that the first and second holders 12 and 22 can rotate and move.

The anastomosis device includes the upper case 32 and the lower case 34. The upper case 32 is disposed over the first and second guide bars 16 and 26. The lower case 34 is disposed under the first and second guide bars 16 and 26. The first and second guide bars 16 and 26 are installed in the inner space provided by the upper case 32 and the lower case 34.

The anastomosis device includes the movement driver 62 and the push bar 64. The movement driver 62 moves forward or rearward in the longitudinal direction of the upper case 32 and the lower case 34. The movement driver 62 is disposed at the front side of the rotation drivers 42 and 44 to be described later, and is moved together with the rotation drivers 42 and 44. In addition, the movement driver 62 surrounds the first and second guide bars 16 and 26 to bring the first and second guide bars 16 and 26 to come close to each other, which will be described later in detail. The rear end of the push bar 64 is connected to the movement driver 62, and moves together with the movement driver 62. Accordingly, the first and second anastomosis rings R1 and R2 fixed to the first and second holders 12 and 22 or coupled by movements of the first and second holders 12 and 22 are removed from the first and second holders 12 and 22.

The anastomosis device includes the rotation drivers 42 and 44 and the lever 40. The rotation drivers 42 and 44 include a lower rotation driver (also denoted by 42) and an upper rotation driver (also denoted by 44). The rotation drivers 42 and 44 are moved forward or rearward in the longitudinal direction of the upper case 32 and the lower case 34 by an operation of the lever 40, and surround the rear ends of the first and second guide bars 16 and 26 to rotate the first and second guide bars 16 and 26, which will be described later in detail. The lever 40 has a ring shape, and an operator's finger is inserted in the lever 40 to conveniently operate the lever 40.

Figure 16:
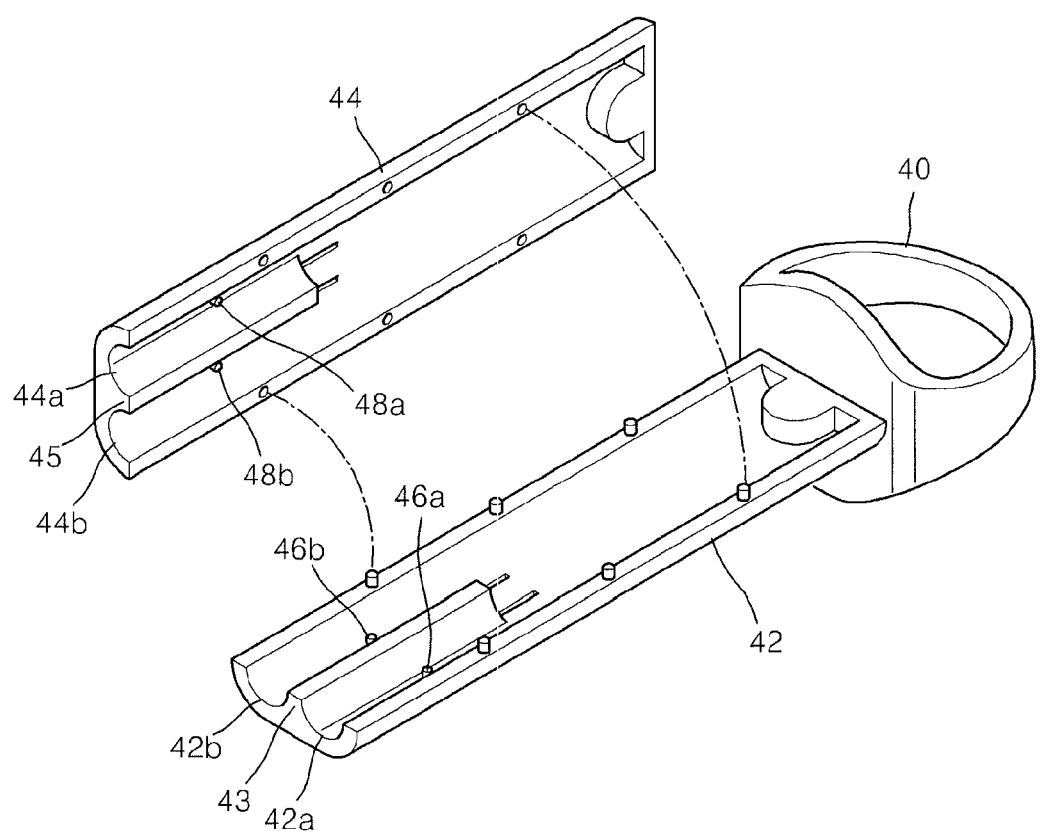
FIG. 16 is a perspective view illustrating a rotation driver and a lever of FIG. 14.

FIG. 16 is a perspective view illustrating the rotation driver and the lever of FIG. 14. Referring to FIG. 16, the rotation drivers 42 and 44 include the lower rotation driver 42 and the upper rotation driver 44, which are coupled to each other. The lower rotation driver 42 is divided into a first lower slot 42a and a second lower slot 42b by a lower middle wall 43. The rear ends of the first and second guide bars 16 and 26 move along the first lower slot 42a and the second lower slot 42b. The upper rotation driver 44 is divided into a first upper slot 44a and a second upper slot 42b by an upper middle wall 45. The rear ends of the first and second guide bars 16 and 26 move along the first upper slot 44a and the second upper slot 44b.

As illustrated in FIG. 16, a first lower guide protrusion 46a and a second lower guide protrusion 46b are disposed on the first and second lower slots 42a and 42b, and a first upper guide protrusion 48a and a second upper guide protrusion 48b are disposed on the first and second upper slots 44a and 44b. The rear end of the first guide bar 16 moves along a first rotation slot formed by the first lower slot 42a and the first upper slot 44a, and the rear end of the second guide bar 26 moves along a second rotation slot formed by the second lower slot 42b and the second upper slot 44b. At this point, the second lower guide protrusion 46b and the second upper guide protrusion 48b move along the second movement groove 27a and the second rotation groove 27b, and the second guide bar 26 can rotate accordingly. The first guide bar 16 rotates in a same manner. This will be described later in detail.

Figure 17:
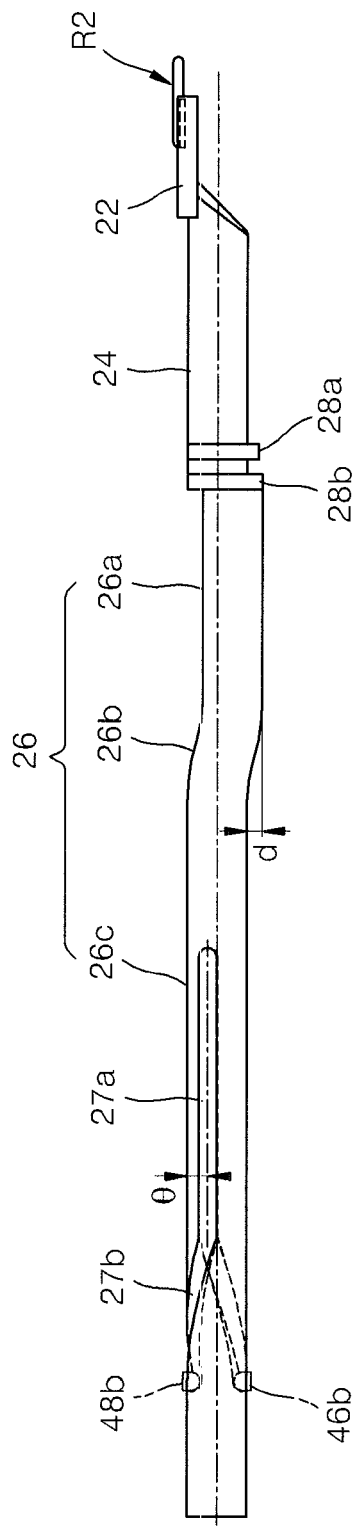
FIGS. 17 through 19 are side views illustrating a second holder, a second connecting bar, and a second guide bar as shown in FIG. 14.
Figure 18:
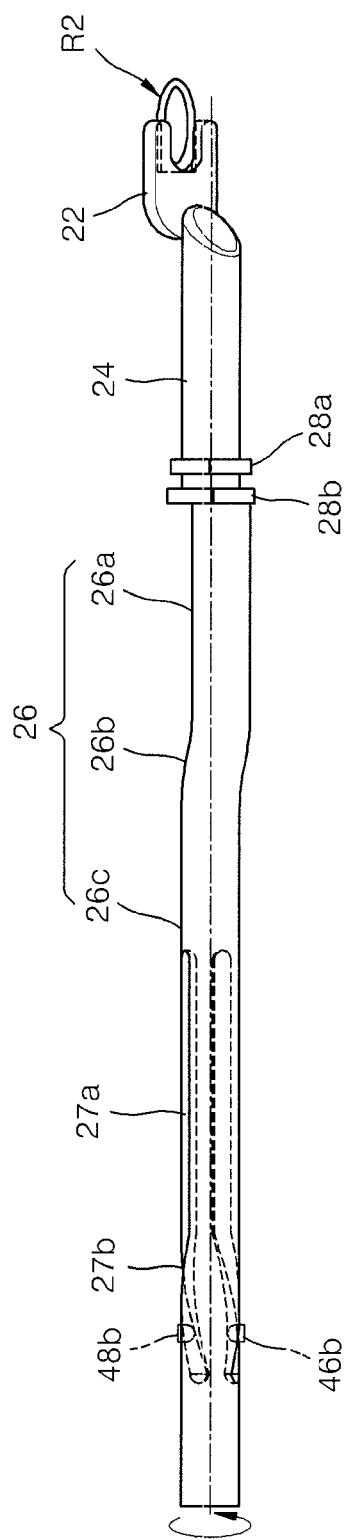
Figure 19:
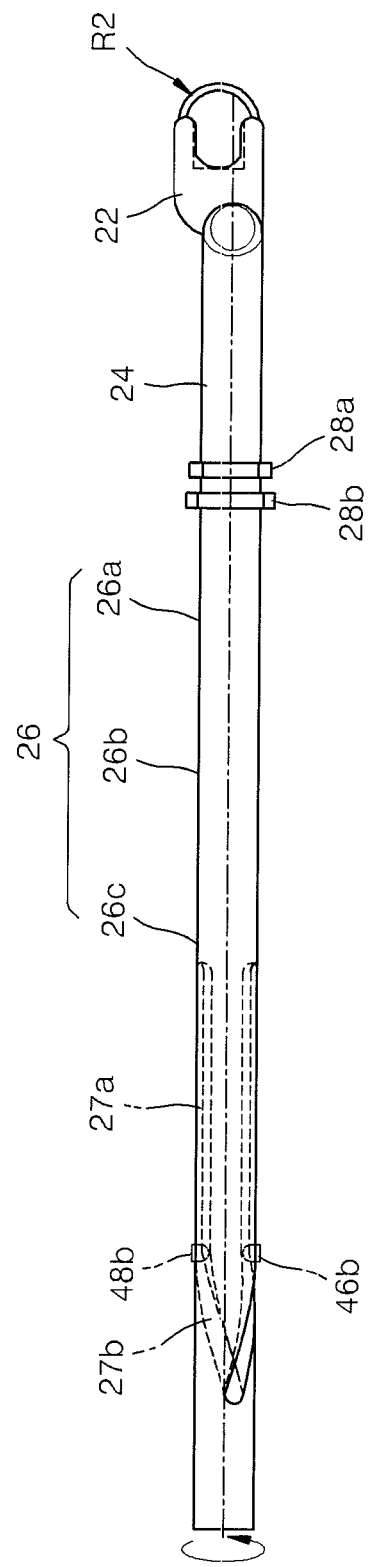

FIGS. 17 through 19 are side views illustrating the second holder, the second connecting bar, and the second guide bar as shown in FIG. 14. The following descriptions of the second holder, the second connecting bar, and the second guide bar are similar to descriptions of the first holder, the first connecting bar, and the first guide bar except that the first holder, the first connecting bar, and the first guide bar are symmetrical to the second holder, the second connecting bar, and the second guide bar with respect to the center of the upper case 32 and the lower case 34. Thus, the descriptions of the first holder, the first connecting bar, and the first guide bar will be omitted here.

Referring to FIG. 17, the second holder 22 is approximately parallel to a ground or is slightly inclined from the ground. At this point, the second anastomosis ring R2 is fixed to the second holder 22 through the open front end of the second holder 22 (release position). The second guide bar 26 includes the second front rod 26a, the second rear rod 26c, and the second connecting rod 26b connecting the second front rod 26a to the second rear rod 26c. As illustrated in FIG. 17, the second slave bar 24 and the second rear rod 26c have the same rotation axis (or central axis). Thus, when the second rear rod 26c rotates, the second slave bar 24 rotates about the same rotation axis as that of the second rear rod 26c.

The second slave bar 24 includes a second front collar 28a and a second rear collar 28b, which are spaced apart from each other. A front wall 36 (refer to FIG. 15) is inserted between the second front collar 28a and the second rear collar 28b. The second front collar 28a and the second rear collar 28b are disposed at the front and rear sides of the front wall 36, respectively, and limit a back-and-forth movement of the second slave bar 24. Thus, the second slave bar 24 can rotate and move on the front wall 36.

The second front rod 26a is disposed eccentrically from the rotation axis of the second rear rod 26c. When the second holder 22 is disposed at the release position, the lower surface of the second front rod 26a protrudes from the rotation axis by a predetermined distance d.

As illustrated in FIG. 17, the second rear rod 26c includes the second movement groove 27a and the second rotation groove 27b. Each of the second movement groove 27a and the second rotation groove 27b is provided in duplicate. One of the second movement grooves 27a and one of the second rotation grooves 27b are displaced from the other of the second movement grooves 27a and the other of the second rotation grooves 27b, respectively, by an angle of about 180° about the rotation axis. The second movement groove 27a extends in the longitudinal direction of the second rear rod 26c. The second rotation groove 27b extends from the rear end of the second movement groove 27a and has a spiral shape that extends in the longitudinal direction of the second rear rod 26c as a whole. As illustrated in FIG. 17, the second rotation groove 27b spirals clockwise to the front side of the second rear rod 26c, and has a predetermined angle θ about the rotation axis (or central axis) of the second rear rod 26c, from the rear end of the second rotation groove 27b to the front end thereof.

As described above, the second lower guide protrusion 46b and the second upper guide protrusion 48b are inserted in the second movement grooves 27a and the second rotation grooves 27b, and move along the second movement grooves 27a and the second rotation grooves 27b according to a back-and-forth movement of the lower rotation driver 42 and the upper rotation driver 44.

Hereinafter, a rotation of the second guide bar 26 will now be described with reference to FIGS. 17 through 19. As illustrated in FIG. 17, when the second holder 22 is disposed at the release position, the second lower guide protrusion 46b and the second upper guide protrusion 48b are disposed in the rear ends of the second rotation grooves 27b.

Then, as the lower rotation driver 42 and the upper rotation driver 44 move forward, the second lower guide protrusion 46b and the second upper guide protrusion 48b move forward together with the lower rotation driver 42 and the upper rotation driver 44, as illustrated in FIG. 18. At this point, the second lower guide protrusion 46b and the second upper guide protrusion 48b move along the second rotation grooves 27b, and thus, the second rear rod 26c rotates counterclockwise (viewed from the left side of FIG. 18). This is because the second lower guide protrusion 46b and the second upper guide protrusion 48b are fixed to the lower rotation driver 42 and the upper rotation driver 44, and the positions of the second rotation grooves 27b (or the second rear rod 26c) are confined by the second lower guide protrusion 46b and the second upper guide protrusion 48b.

As illustrated in FIG. 19, when the second lower guide protrusion 46b and the second upper guide protrusion 48b are disposed in the front ends of the second rotation grooves 27b, the second rear rod 26c rotates by the above-described angle θ, and the second holder 22 moves from the release potions of FIG. 17 to the standby position.

Figure 20:
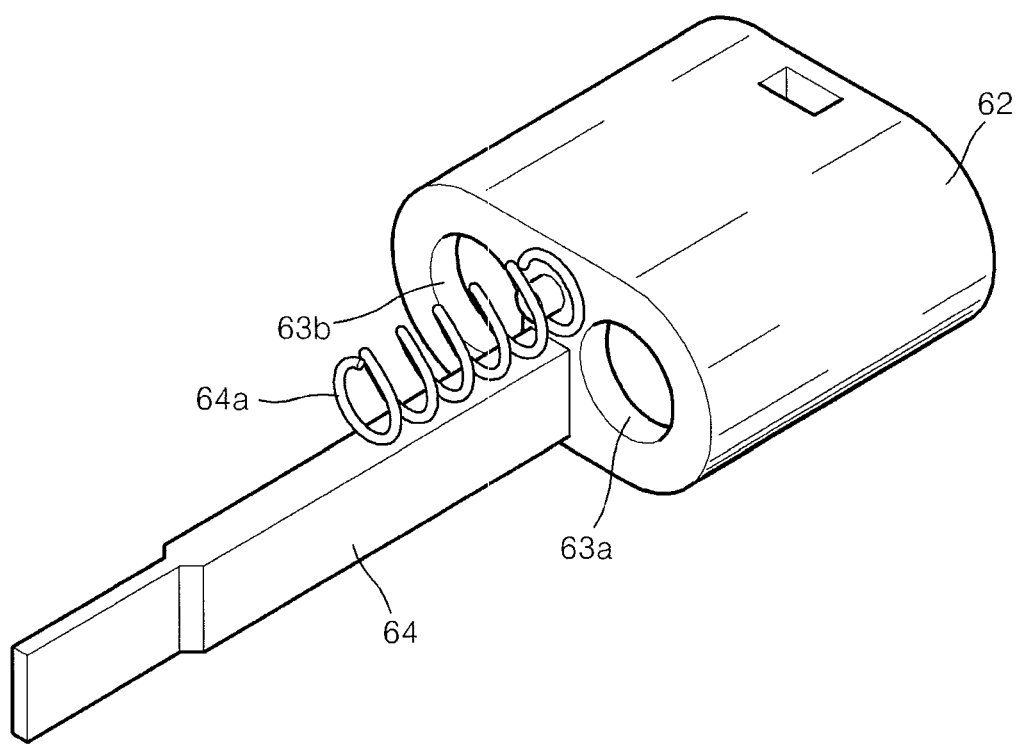
FIG. 20 is a perspective view illustrating a movement driver and a push bar of FIG. 15.
Figure 21:
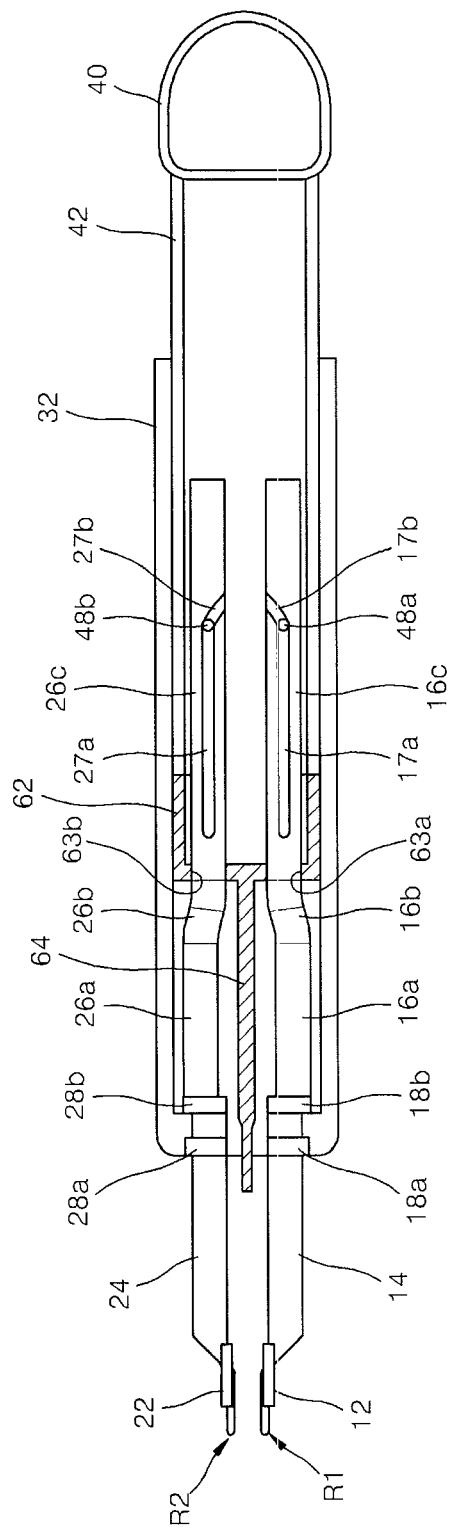
FIGS. 21 and 22 are views illustrating movements of a first guide bar and a second guide bar according to a movement of a movement driver according to an embodiment of the present invention.
Figure 22:
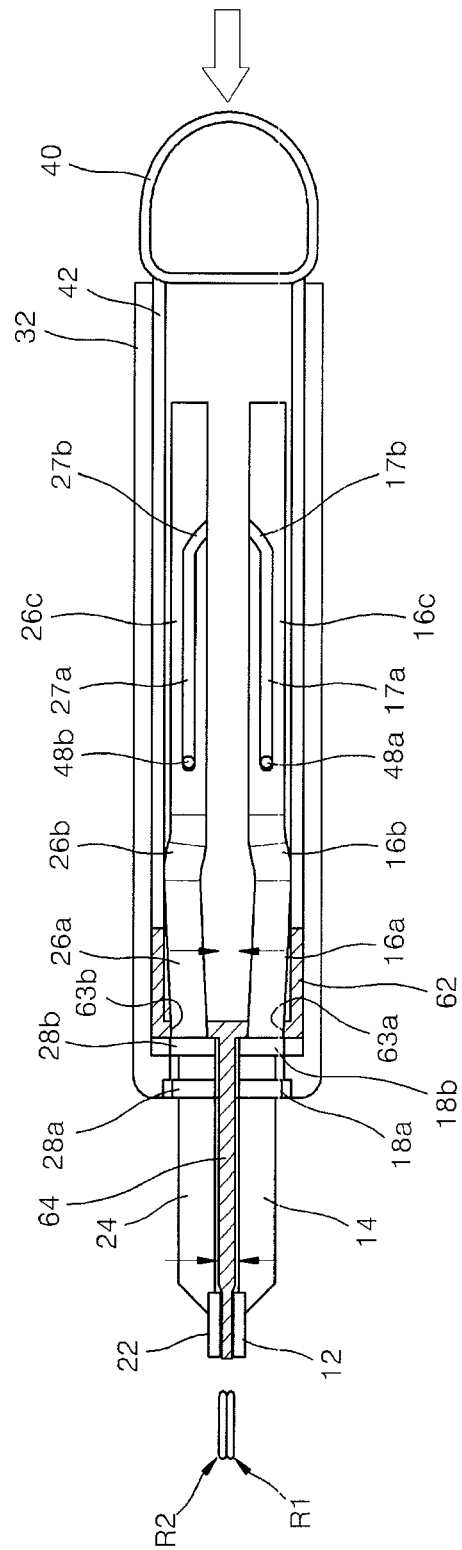

FIG. 20 is a perspective view illustrating the movement driver and the push bar of FIG. 15. FIGS. 21 and 22 are views illustrating movements of a first guide bar and a second guide bar according to a movement of a movement driver. Referring to FIG. 20, the movement driver 62 includes a first movement slot 63a and a second movement slot 63b. The first and second guide bars 16 and 26 are inserted in the first and second movement slots 63a and 63b, and move along the first and second movement slots 63a and 63b.

The rear end of the push bar 64 is connected to the movement driver 62, and moves together with the movement driver 62. Accordingly, the first and second anastomosis rings R1 and R2 fixed to the first and second holders 12 and 22 or coupled by movements of the first and second holders 12 and 22 are removed from the first and second holders 12 and 22. An elastic body 64a (for example, a coil spring) is disposed over the push bar 64. An end of the elastic body 64a contacts the movement driver 62, and the other end thereof contacts the front wall of the upper case 32. The elastic body 64a is compressed by the movement driver 62 moved forward. After an anastomosis, the elastic body 64a uses its elastic force to return the movement driver 62 to its original position.

Hereinafter, movements of the first and second front rods 16a and 26a will now be described with reference to FIGS. 21 and 22.

As described above, when the second lower guide protrusion 46b and the second upper guide protrusion 48b arrive at the front ends of the second rotation grooves 27b, the first and second holders 21 and 22 are disposed at the standby position. Referring to FIG. 21, the first and second front rods 16a and 26a spread wider than the first and second rear rods 16c and 26c, and the first and second connecting rods 16b and 26b extend forward and inclined outward. At this point, the first and second movement slots 63a and 63b of the movement driver 62 are disposed at the front ends of the first and second rear rods 16c and 26c.

Referring to FIG. 22, when the lever 40 is pushed forward, the movement driver 62 and the lower rotation driver 42 move forward. At this point, the first and second movement slots 63a and 63b move forward to sequentially press the side surfaces of the first and second connecting rods 16b and 26b, and the outer surfaces of the first and second front rods 16a and 26a. Thus, as illustrated in FIG. 22, the front ends of the first and second front rods 16a and 26a come close to each other, which is depicted with arrows. At this point, the first and second connecting rods 16b and 26b are bent by the pressing of the first and second movement slots 63a and 63b. To this end, the first and second connecting rods 16b and 26b may be formed of polymer (for example, PE-based material) having small elasticity, or a metal. When the movement driver 62 returns its original position, the front ends of the first and second front rods 16a and 26a also return their original positions. Each of the first and second guide bars 16 and 26 may be provided in the form of a single body, and be formed of polymer having small elasticity or a metal, as described above.

The front ends of the first and second slave bars 14 and 24 come close to each other, which is depicted with arrows, and the first and second holders 12 and 22 come close to each other accordingly (close position). Accordingly, the first and second anastomosis rings R1 and R2 fixed to the first and second holders 12 and 22 come close to each other and couple to each other.

Then, the push bar 64 connected to the movement driver 62 is inserted between the first and second holders 12 and 22. Accordingly, the first and second anastomosis rings R1 and R2 coupled by the movements of the first and second holders 12 and 22 are removed from the first and second holders 12 and 22.

Figure 23:
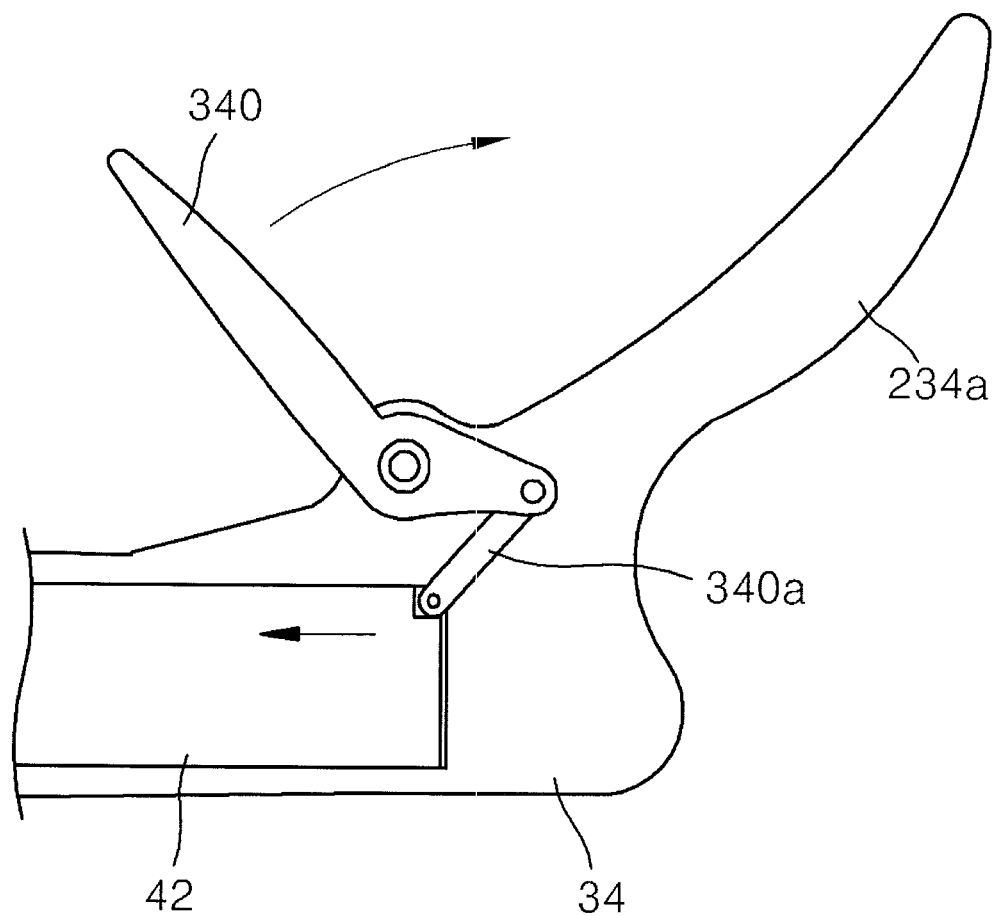
FIGS. 23 through 25 are various modifications of a lever according to embodiments of the present invention.
Figure 24:
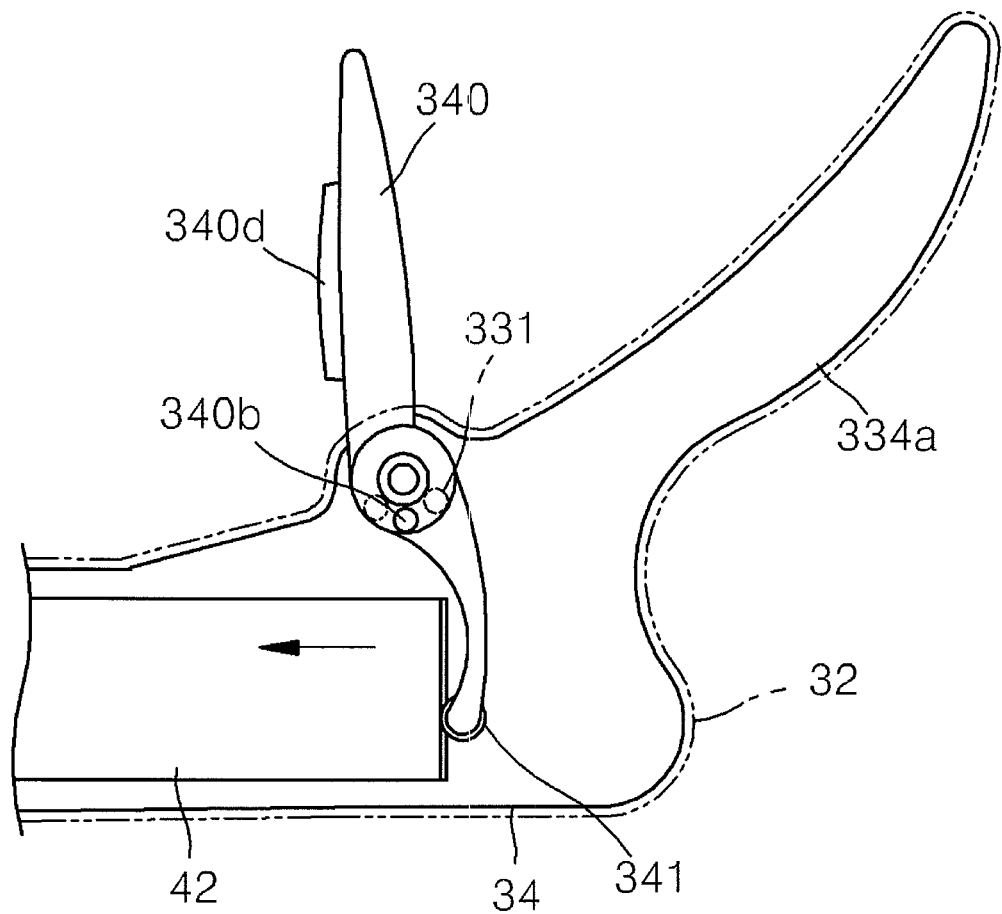
Figure 25:
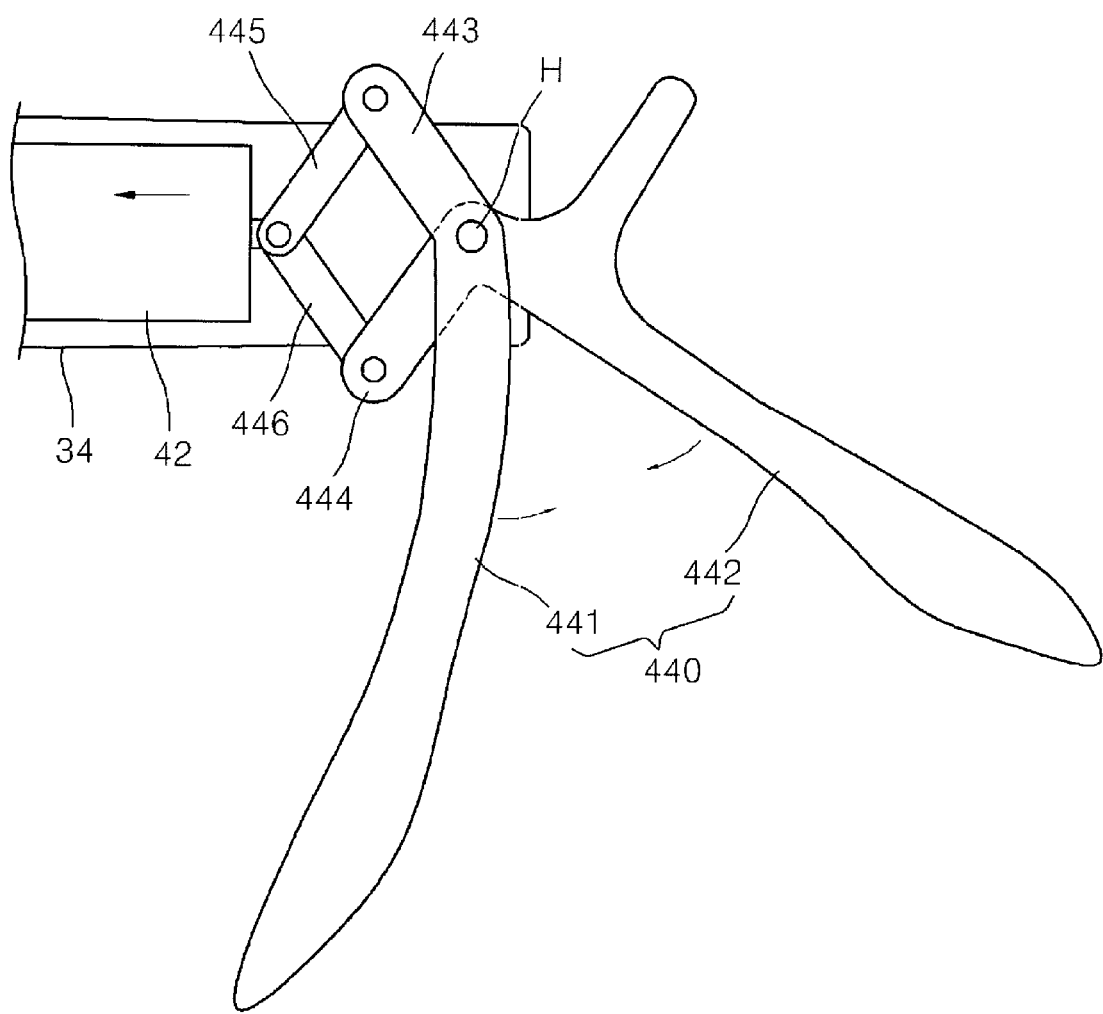
Figure 26:
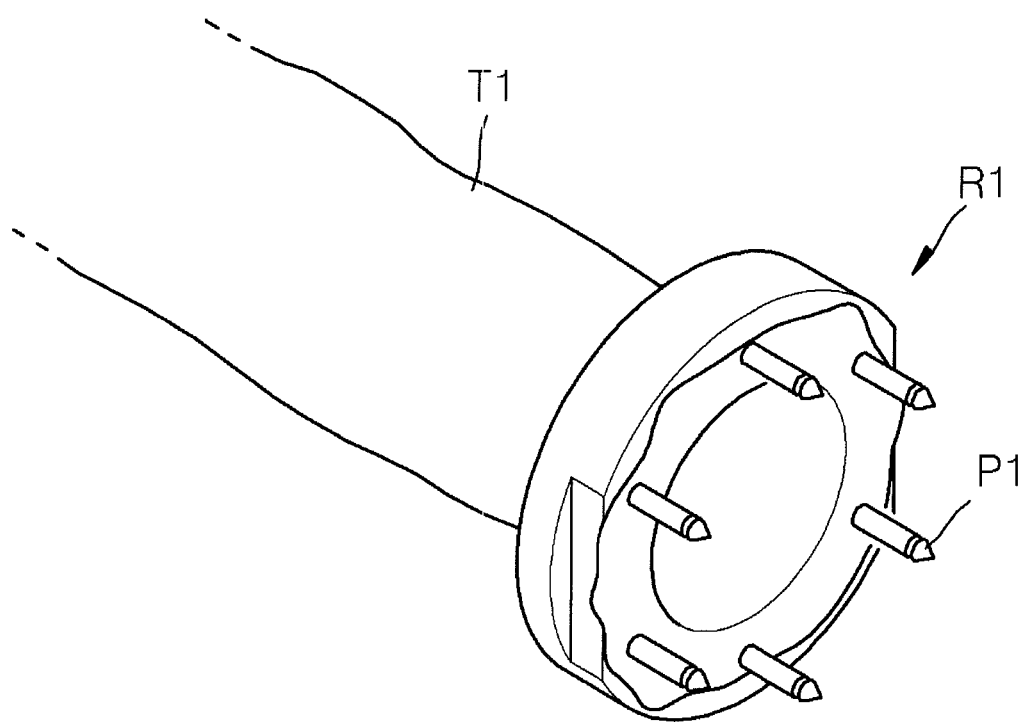
FIG. 26 is a perspective view illustrating an anastomosis ring installed on a tubular body structure in the related art.
Figure 27:
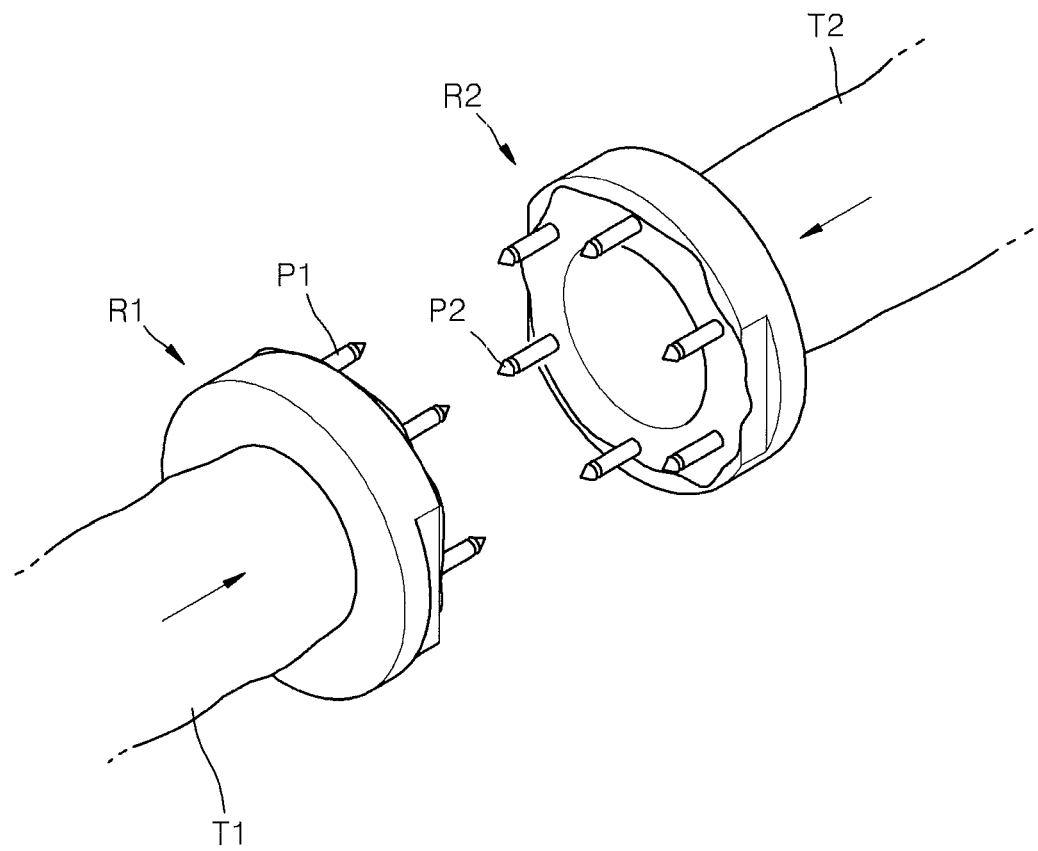
FIG. 27 is a perspective view illustrating an anastomosis using anastomosis rings in the related art.

FIGS. 23 through 25 are various modifications of a lever according to embodiments of the present invention. According to the previous embodiments, the lever 40 is rotated to move the driver 160 forward as illustrated in FIG. 2, or the lever 40 is pushed to move the lower rotation driver 42 and the upper rotation driver 44 forward as illustrated in FIG. 13. However, according to the current embodiments, the driver 160 can be moved forward using various other methods.

Referring to FIG. 23, a handle 234a may be installed on the lower case 34, and a trigger 340 may be installed at the front side of the handle 234a. The trigger 340 is rotatably fixed to the lower case 34, and an end of the trigger 340 may be connected to the lower rotation driver 42 through a link 340a.

When an operator holding the handle 234a pulls the trigger 340, the trigger 340 rotates, and thus, the link 340a moves the lower rotation driver 42 forward. As such, a trigger method uses the principal of a lever to produce a large force from a small force. Thus, an accident due to an operation's excessive force can be prevented.

Referring to FIG. 24, a pressing member 341, for example, formed of rubber is installed on an end of the trigger 340. In this case, when the trigger 340 is pulled, the pressing member 341 directly presses the rear end of the lower rotation driver 42 to move the lower rotation driver 42 forward.

The upper case 32 disposed over the lower case 34 may include fixing holes 331 around a rotation center of the trigger 340. A stopper 340b protruding from the trigger 340 is selectively inserted in one of the fixing holes 331 to limit a rotation of the trigger 340. Accordingly, a forward movement of the lower rotation driver 42 can be temporarily stopped, thereby stopping an anastomosis or preventing the lower rotation driver 42 from temporarily moving rearward.

The stopper 340b can be controlled with a safety lever 340d of the trigger 340. The safety lever 340d may be pressed to remove the stopper 340b from the fixing hole 331.

Referring to FIG. 25, triggers 440 are rotatably fixed to the lower case 34 through a hinge H, and include triggers 441 and 442. Links 443 and 444 are connected to the triggers 441 and 442, respectively. Further, the links 443 and 444 may be connected to the lower rotation driver 42 through auxiliary links 445 and 446, respectively. An operator can press the triggers 440 to rotate the links 443 and 444 and the auxiliary links 445 and 446, thereby moving the lower rotation driver 42 forward.

According to the embodiments, tubular body structures such as blood vessels and intestines can be efficiently and quickly connected to each other through an anastomosis. In particular, since the anastomosis rings can be coupled to each other through a single process a defect due to an unnecessary process can be prevented.

The above-disclosed subject matter is to be considered illustrative and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An anastomosis device comprising:
a first head holding a first anastomosis ring;
a second head holding a second anastomosis ring;
a first guide bar connected to the first head and switching a release position and a standby position to each other, wherein the first and second anastomosis rings are directed upward at the release position, and the first and second anastomosis rings face each other at the standby position, and the first guide bar includes a first rotation groove that extends in a spiral shape approximately in a longitudinal direction of the first guide bar;
a second guide bar connected to the second head and switching the release position and the standby position to each other, wherein the second guide bar includes a second rotation groove that extends in a spiral shape approximately in a longitudinal direction of the second guide bar; and
a rotation driver moving approximately in a parallel direction to the first and second guide bars and including a first guide protrusion and a second guide protrusion, which move along the first and second rotation grooves, respectively,
wherein the first and second guide bars switch the standby position and the release position to each other according to the movements of the first and second guide protrusions along the first and second rotation grooves.

2. The anastomosis device of claim 1, wherein the rotation driver comprises a first rotation slot and a second rotation slot in which rear ends of the first and second guide bars are inserted, respectively, and
the first and second guide protrusions are installed on the first and second rotation slots to move along the first and second rotation grooves.

3. The anastomosis device of claim 1, wherein the first guide bar comprises: a first front rod and a first rear rod, which are approximately parallel to each other; and a first connecting rod that connects the first front rod to the first rear rod,
the second guide bar comprises: a second front rod and a second rear rod, which are approximately parallel to each other; and a second connecting rod that connects the second front rod to the second rear rod, and
the anastomosis device further comprises a movement driver that includes a first push slot and a second push slot in which the first and second guide bars are inserted,
wherein the movement driver moves along the first and second connecting rods to switch a close position and the standby position to each other,
the first and second heads come close to each other to couple the first and second anastomosis rings to each other at the close position, and
the first and second heads go away from each other to separate the first and second anastomosis rings from each other at the standby position.

4. The anastomosis device of claim 3, wherein the first rear rod and the first head have an identical first rotation axis,
the first front rod is eccentrically disposed from the first rotation axis,
the second rear rod and the second head have an identical second rotation axis, and
the second front rod is eccentrically disposed from the second rotation axis.

5. The anastomosis device of claim 3, wherein the first connecting rod is inclined outward to the first front rod when the first guide bar is disposed at the standby position, and
the second connecting rod is inclined outward to the second front rod when the second guide bar is disposed at the standby position.

6. The anastomosis device of claim 3, wherein the first rear rod comprises the first rotation groove and a first movement groove that extends from the first rotation groove approximately in a longitudinal direction of the first rear rod, and
the second rear rod comprises the second rotation groove and a second movement groove that extends from the second rotation groove approximately in a longitudinal direction of the second rear rod.

7. The anastomosis device of claim 6, wherein a length of the first rotation groove and the first movement groove is approximately equal to a travelling distance of the rotation driver and the movement driver.

8. The anastomosis device of claim 3, wherein the movement driver comprises a push bar that removes the first and second anastomosis rings from the first and second heads.

9. The anastomosis device of claim 3, wherein the connecting rod is formed of an elastic material.

10. The anastomosis device of claim 1, wherein the first guide bar comprises: a first front rod and a first rear rod, which are approximately parallel to each other; and a first connecting rod that connects the first front rod to the first rear rod,
the second guide bar comprises: a second front rod and a second rear rod, which are approximately parallel to each other; and a second connecting rod that connects the second front rod to the second rear rod, and
the rotation driver comprises a first rotation slot and a second rotation slot in which rear ends of the first and second guide bars are inserted, respectively, wherein the first and second guide protrusions moving along the first and second rotation grooves are installed on the first and second rotation slots, and
the rotation driver further comprises a movement driver that moves along the first and second connecting rods to switch a close position and the standby position to each other, wherein the first and second heads come close to each other to couple the first and second anastomosis rings to each other at the close position, and the first and second heads go away from each other to separate the first and second anastomosis rings from each other at the standby position.

11. The anastomosis device of claim 10, wherein the first rear rod and the first head have an identical first rotation axis,
the first front rod is eccentrically disposed from the first rotation axis,
the second rear rod and the second head have an identical second rotation axis, and
the second front rod is eccentrically disposed from the second rotation axis.

12. The anastomosis device of claim 11, wherein the first guide bar comprises a first movement groove extending from the first rotation groove and approximately parallel to the first rotation axis, and
the second guide bar comprises a second movement groove extending from the second rotation groove and approximately parallel to the second rotation axis.

13. The anastomosis device of claim 10, wherein the first connecting rod is inclined outward to the first front rod when the first guide bar is disposed at the standby position, and
the second connecting rod is inclined outward to the second front rod when the second guide bar is disposed at the standby position.

14. The anastomosis device of claim 10, wherein the first guide bar comprises a first movement groove extending from the first rotation groove, and the second guide bar comprises a second movement groove extending from the second rotation groove, wherein the first movement groove includes a first front groove parallel to the first front rod, a first connecting groove parallel to the first connecting rod, and a first rear groove parallel to the first rear rod, and the second movement groove includes a second front groove parallel to the second front rod, a second connecting groove parallel to the second connecting rod, and a second rear groove parallel to the second rear rod.

* * * * *